(12) United States Patent
Frach et al.

(10) Patent No.: US 8,395,127 B1
(45) Date of Patent: Mar. 12, 2013

(54) DIGITAL SILICON PHOTOMULTIPLIER FOR TOF PET

(75) Inventors: Thomas Frach, Aachen (DE); Gordian Prescher, Cologne (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 464 days.

(21) Appl. No.: 12/351,033

(22) Filed: Jan. 9, 2009

Related U.S. Application Data

(63) Continuation-in-part of application No. 11/467,670, filed on Aug. 28, 2006, now Pat. No. 7,723,694, which is a continuation of application No. PCT/IB2006/051089, filed on Apr. 10, 2006.

(60) Provisional application No. 60/682,246, filed on May 18, 2005, provisional application No. 60/674,034, filed on Apr. 22, 2005.

(51) Int. Cl.
*G01T 1/208* (2006.01)

(52) U.S. Cl. .......... 250/370.11; 250/370.08; 250/370.14

(58) Field of Classification Search ............. 250/370.08, 250/370.11, 370.14
See application file for complete search history.

(56) References Cited

U.S. PATENT DOCUMENTS

| | | | | |
|---|---|---|---|---|
| 2,477,802 | A * | 8/1949 | Herzog et al. | 250/374 |
| 4,720,799 | A * | 1/1988 | Woithe et al. | 702/55 |
| 5,449,897 | A | 9/1995 | Bertelsen et al. | |
| 5,532,122 | A * | 7/1996 | Drukier | 435/5 |
| 5,548,112 | A * | 8/1996 | Nakase et al. | 250/214 C |
| 5,585,637 | A | 12/1996 | Bertelsen et al. | |
| 6,114,703 | A | 9/2000 | Levin et al. | |
| 6,313,459 | B1 * | 11/2001 | Hoffe et al. | 250/214 R |
| 6,448,559 | B1 | 9/2002 | Saoudi et al. | |
| 6,459,085 | B1 * | 10/2002 | Chang et al. | 250/370.11 |
| 6,541,752 | B2 | 4/2003 | Zappa et al. | |
| 6,781,133 | B2 | 8/2004 | Karplus et al. | |
| 6,909,672 | B2 | 6/2005 | Rao | |
| 7,045,789 | B2 | 5/2006 | Ogawa et al. | |
| 2002/0099511 | A1 * | 7/2002 | Matsushita et al. | 702/104 |
| 2004/0245592 | A1 * | 12/2004 | Harmon et al. | 257/438 |
| 2005/0012033 | A1 | 1/2005 | Stern et al. | |
| 2005/0029453 | A1 * | 2/2005 | Allen et al. | 250/332 |

FOREIGN PATENT DOCUMENTS

| | | |
|---|---|---|
| EP | 0706065 A1 | 10/1996 |
| JP | 9005439 A | 1/1997 |
| JP | 2002116256 A | 4/2002 |
| JP | 2004117356 A | 4/2004 |
| WO | 2004044613 A2 | 5/2004 |
| WO | 2004095068 A1 | 11/2004 |
| WO | 2004099865 A1 | 11/2004 |

(Continued)

OTHER PUBLICATIONS

Fries et al. A small animal PET prototype based on LSO crystals read out by avalanche photodiodes, Nuclear Instruments and Methods in Physics Research Section A, vol. 387, No. 1-2 (Mar. 1997), pp. 220-224.*

(Continued)

*Primary Examiner* — David Porta
*Assistant Examiner* — Shun Lee

(57) ABSTRACT

A radiation detector includes an array of detector pixels each including an array of detector cells. Each detector cell includes a photodiode biased in a breakdown region and digital circuitry coupled with the photodiode and configured to output a first digital value in a quiescent state and a second digital value responsive to photon detection by the photodiode. Digital triggering circuitry is configured to output a trigger signal indicative of a start of an integration time period responsive to a selected number of one or more of the detector cells transitioning from the first digital value to the second digital value. Readout digital circuitry accumulates a count of a number of transitions of detector cells of the array of detector cells from the first digital state to the second digital state over the integration time period.

21 Claims, 13 Drawing Sheets

FOREIGN PATENT DOCUMENTS

WO 2004111681 A1 12/2004
WO 2005017598 A1 2/2005

OTHER PUBLICATIONS

Andreev et al. A high-granularity scintillator calorimeter readout with silicon photomultipliers, Nuclear Instruments and Methods in Physics reasearch A, vol. 540 (Jan. 2005), pp. 368-380.*

Garutti Dedicated front-end electronics for an ILC prototype hadronic calorimeter with SiPM readout, 2005 IEEE Nuclear Science Symposium Conference Record (Oct. 2005), pp. 1499-1502.*

Aull, B.F., et al.; Geiger-Mode Avalanche Photodiodes for Three-Dimensional Imaging; 2002; Lincoln Laboratory Journal; 13(2)335-350.

Georgievskya, E.A., et al.; The solid-state silicon photomultiplier for a wide range of applications; 2003; Proc. of SPIE; 5126:37-42.

Golovin, V., et al.; Novel type of avalanche photodetector with Geiger mode operation; 2004; Nuclear Instruments and Methods in Physics Research A 518: 560-564.

Sadygov, Z.Y., et al.; Avalanche Semiconductor Radiation Detectors; 1996; IEEE Trans. on Nuclear Science; 63(3) 1009-1013.

Saveliev, V.; The recent development and study of silicon photomultiplier; 2004; Nuclear Instruments and Methods in Physics Research A 535:528-532.

Herbert, D. J., et al.; First results of scintillator readout with silicon photomultiplier; 2004; IEEE Nuclear Science Symposium Conf. Record; pp. 4185-4189.

Otte, A. N., et al.; New results from a test of silicon photomultiplier as readout for PET; 2004; IEEE Nuclear Science Symposium Conf. Record; pp. 3738-3742.

Buzhan, P., et al.; An Advanced Study of Silicon Photomultiplier; 2002; Advanced Technology Particle Physics Proceedings of the 7th International Conference on ICATPP7; World Scientific Publishing Co.; pp. 717-728.

* cited by examiner

DIGITAL SILICON PHOTOMULTIPLIER FOR TOF PET

CROSS REFERENCE TO RELATED APPLICATIONS

This application is a continuation-in-part of U.S. Ser. No. 11/467,670 filed Aug. 28, 2006 which is a continuation of PCT application number PCT/IB2006/051089 filed Apr. 10, 2006 which claims the benefit of U.S. provisional application Ser. No. 60/674,034 filed Apr. 22, 2005 and U.S. provisional application Ser. No. 60/682,246 filed May 18, 2005. U.S. Ser. No. 11/467,670 filed Aug. 28, 2006 is incorporated herein by reference in its entirety. U.S. published application 2008/0203309 A1 published Aug. 28, 2008 (corresponding to U.S. Ser. No. 11/467,670) is incorporated herein by reference in its entirety. PCT application no. PCT/IB2006/051089 is incorporated herein by reference in its entirety. PCT publication WO 2006/111883 A2 published Oct. 26, 2006 (corresponding to PCT/IB2006/051089) is incorporated herein by reference in its entirety. U.S. provisional application Ser. No. 60/674,034 filed Apr. 22, 2005 is incorporated herein by reference in its entirety. U.S. provisional application Ser. No. 60/682,246 filed May 18, 2005 is incorporated herein by reference in its entirety.

BACKGROUND

The following relates to the radiation detection arts. It particularly relates to high-speed radiation detectors for positron emission tomography (PET), especially time-of-flight (TOF) PET, and will be described with particular reference thereto. However, the following relates more generally to radiation detectors for single photon emission computed tomography (SPECT), computed tomography (CT), and so forth, as well as to high-speed radiation detectors for other applications such as astronomy.

In conventional PET, a radiopharmaceutical is administered to a human patient or other imaging subject. The radiopharmaceutical produces radiation decay events that emit positrons, which travel a very short distance before rapidly interacting with an electron of the surrounding imaging subject in an electron-positron annihilation event to produce two oppositely directed gamma rays. The gamma rays are detected by radiation detectors surrounding the imaging subject as two substantially simultaneous radiation detection events that define a line of response (LOR) therebetween. Typically, the radiation detectors include scintillators that produce a burst or scintillation of light responsive to each gamma ray detection, and an array of photomultiplier tubes (PMT's) optically coupled with the scintillators that convert the light bursts into corresponding electrical signals. In some PET scanners, the PMT's are replaced by photodiodes that produce analog electrical currents proportional to the intensity of the light bursts.

Although the gamma rays are detected "substantially simultaneously", if one of the two involved radiation detectors is closer to the electron-positron annihilation event than the other radiation detector, then there will be a small time difference between the two radiation detection events. Since gamma rays travel at the speed of light, this time difference between detections is typically around a few nanoseconds or less. In TOF-PET, the radiation detectors operate at sufficiently high speed to enable measurement of this small time-of-flight difference, which is then used to localize the electron-positron annihilation event along the LOR.

Accordingly, for TOF-PET the radiation detectors should have sub-nanosecond temporal resolution. PMTs are generally fast enough to perform TOF-PET imaging; however, PMTs are bulky, require high voltage biasing, and are not well-suited for small pixel sizes desirable for high resolution. Conventional photodiodes are fast enough for TOF-PET, but lack internal amplification, leading to poor signal-to-noise ratios. To get sufficient signal with a conventional photodiode, a charge-sensitive amplifier is typically employed to integrate the signal, which limits the bandwidth. Avalanche photodiodes can also be used; however, avalanche photodiodes typically suffer from high noise levels and high temperature and bias sensitivity in the gain.

To address these difficulties, silicon photomultiplier (SiPM) detectors have been proposed, for example in: E. A. Georgievskya et al., "The solid state silicon photomultiplier for a wide range of applications", 17$^{th}$ Intl Conf. on Photoelectronics and Night Vision Devices, Proceedings of SPIE vol. 5126 (2003); Golovin et al., "Novel type of avalanche photodetector with Geiger mode operation", Nuclear Instruments & Methods in Physical Research A, volume 518, pages 560-64 (2004). These SiPM detectors use a pixelated array of small avalanche photodiodes biased in the breakdown region and interconnected in parallel. The output is the analog sum of the currents of parallel-interconnected avalanche photodiodes operating in limited Geiger-mode. Each detected photon in the SiPM detector adds on the order of $10^6$ electrons to the output current of the SiPM. The Geiger discharge responsive to photon detection is fast, providing sharp rising edges of the signal that facilitate precise time measurements. Energy- and temporal-resolution scales with $1/\sqrt{N}$ where N is the number of firing cells.

The SiPM device has certain disadvantages. The analog current produced by a photon detection is affected by bias voltage, operating temperature, and critical circuit parameters such as the quenching resistance value. These factors can change the analog current produced by each photon detection, thus limiting the energy resolution of the SiPM. The analog configuration also has the disadvantages of producing high dark counts and allowing faulty avalanche photodiodes to substantially limit detector device manufacturing yield.

The following contemplates improved apparatuses and methods that overcome the aforementioned limitations and others.

BRIEF SUMMARY

According to one aspect, a detector pixel is disclosed for use in conjunction with a scintillator that converts a radiation particle to a burst of light. An array of detector cells is provided. Each detector cell includes a photodiode biased in a breakdown region and digital circuitry coupled with the photodiode. The digital circuitry is configured to output a first digital value in a quiescent state and a second digital value responsive to detection of a photon by the photodiode. Digital triggering circuitry is configured to output a trigger signal indicative of a start of an integration time period responsive to a selected number of one or more of the detector cells transitioning from the first digital value to the second digital value. Readout digital circuitry accumulates a count of a number of transitions of detector cells of the array of detector cells from the first digital state to the second digital state over the integration time period.

In some embodiments, digital timestamp circuitry is configured to output a digital timestamp associated with the count. The digital timestamp is based on a time of the trigger signal relative to a time reference signal.

According to another aspect, a radiation detector includes a scintillator and an array of detector pixels as set forth in the previous paragraph arranged to receive bursts of light produced by the scintillator in response to received radiation. According to another aspect, a time-of-flight positron emission tomography (TOF-PET) imaging system is disclosed. A plurality of radiation detectors as set forth in the previous two paragraphs are disposed to detect gamma rays emitted from an imaging region. Gamma ray pair detection circuitry identifies two substantially simultaneous gamma ray detections by two of the radiation detectors. A line of response processor determines a spatial line of response connecting the two gamma ray detections. A time of flight processor localizes a positron-electron annihilation event along the line of response based on a time difference between the two substantially simultaneous gamma ray detections.

According to another aspect, a method is performed in conjunction with a scintillator that converts a radiation particle to a burst of light. Digital circuitry is switched from a first digital value to a second digital value responsive to detection of a photon by a photodiode biased in a breakdown region by the digital circuitry to define a switching event. A trigger signal indicative of a start of an integration time period is generated responsive to a selected number of one or more said switching events associated with a plurality of said photodiodes. A count of switching events associated with the plurality of said photodiodes is accumulated over the integration time period.

In some embodiments, the method further includes generating a digital timestamp associated with the accumulating over the integration time period. The digital timestamp is based on a time of generation of the trigger signal and a reference time signal.

According to another aspect, a radiation detector is disclosed, including a scintillator and circuitry for performing the method set forth in the previous paragraph.

One advantage resides in providing high data-rate radiation detection for TOF-PET, single photon emission computed tomography (SPECT), transmission computed tomography (CT), astronomy, and other applications.

Another advantage resides in providing a digital radiation detector output.

Another advantage resides in providing a digitally timestamped detector output.

Another advantage resides in providing improved spatial detector resolution.

Another advantage resides in improved detector device manufacturing yield with low sensitivity to temperature, bias voltage, and process parameters.

Numerous additional advantages and benefits will become apparent to those of ordinary skill in the art upon reading the following detailed description.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

DETAILED DESCRIPTION OF THE PREFERRED EMBODIMENTS

Figure 1:
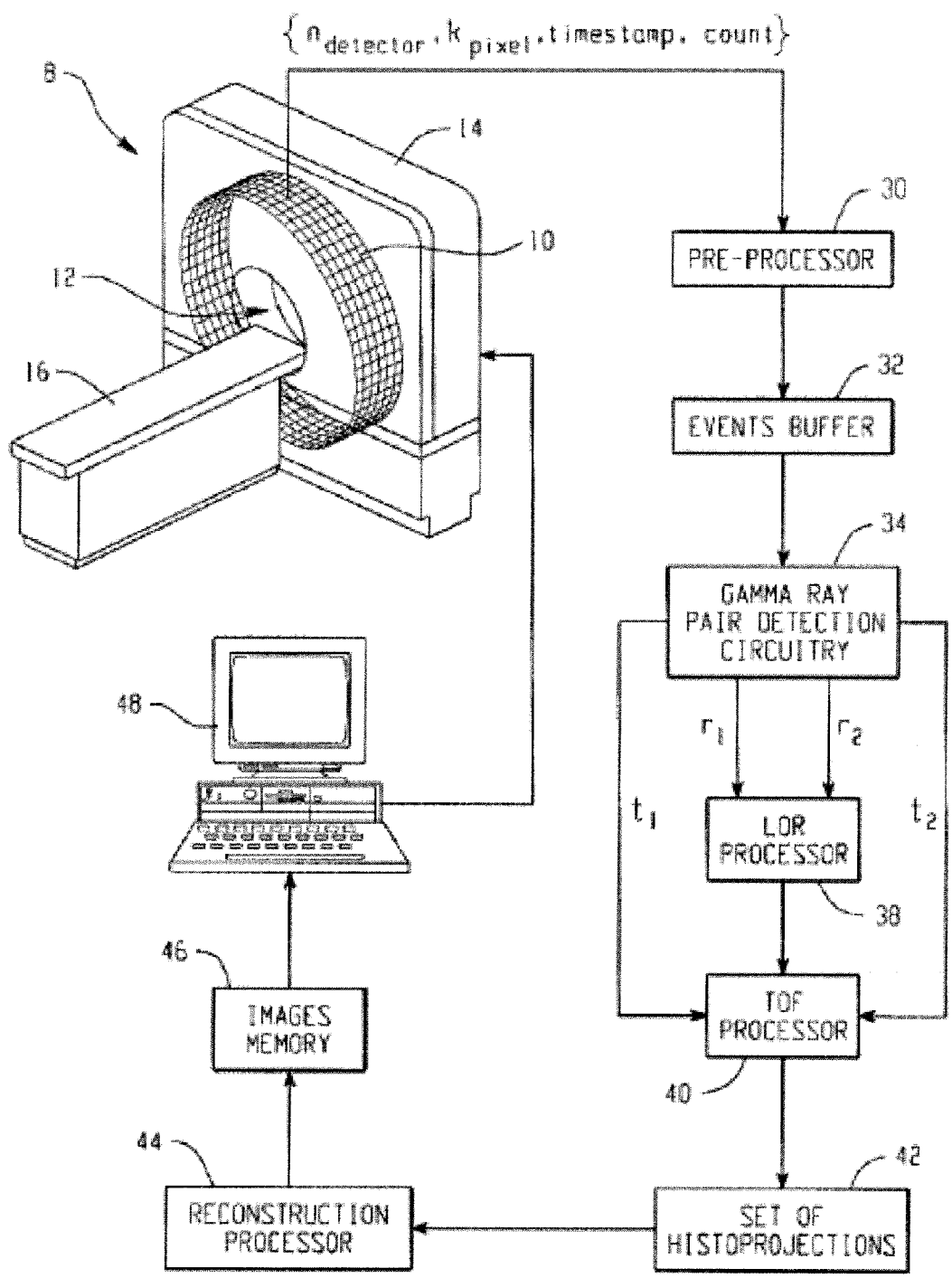
FIG. 1 diagrammatically shows a TOF-PET system employing high-speed pixelated digital radiation detectors.

With reference to FIG. 1, a time-of-flight positron emission tomography (TOF-PET) scanner 8 includes a plurality of radiation detectors 10 arranged to view an imaging region 12. In FIG. 1, the plurality of radiation detectors 10 are arranged in several rings of detectors along an axial direction; however, other arrangements of radiation detectors can be used. Moreover, it is to be appreciated that the plurality of radiation detectors 10 is diagrammatically illustrated; typically the radiation detectors are housed within a housing 14 of the scanner 8 and thus are not visible from the outside, and typically each ring of radiation detectors includes hundreds or thousands of radiation detectors. In some PET scanners, only a single ring of radiation detectors is provided, in others, two, three, four, five, or more rings of radiation detectors are provided. It should be appreciated that detector heads can be used in place of the detector ring structure shown in the Figures. The TOF-PET scanner 8 includes a couch 16 or other support for positioning a human patient or other imaging subject in the imaging region 12. Optionally, the couch 16 is linearly movable in the axial direction generally transverse to the rings of radiation detectors 10 to facilitate acquisition of three-dimensional imaging data. Additionally or alternatively, the imaging subject can be held stationary, and the plurality of rings of radiation detectors used to acquire three-dimensional TOF-PET imaging data. In yet other embodiments, only a single ring of detectors is provided, the imaging subject remains stationary, and the resulting image is two-dimensional.

A suitable radiopharmaceutical is administered to the patient or other imaging subject prior to initiation of TOF-PET imaging. The radiopharmaceutical includes a radioactive substance that undergoes radioactive decay events that emit positrons. The positrons rapidly annihilate with nearby electrons of the imaging subject. The resulting positron-electron annihilation event produces two oppositely directed gamma rays having energies of 511 keV. The gamma rays travel at the speed of light, i.e. $\sim 3 \times 10^8$ meters/sec. Since the imaging region 12 typically has a diameter or other characteristic dimension of about two meters or less, the time-of-flight for a gamma particle from the position of the positron-electron annihilation event to one of the detectors of the plurality of radiation detectors 10 is about a few nanoseconds or less. Thus, the two oppositely directed gamma rays strike two of the radiation detectors substantially simultaneously.

Figure 2:
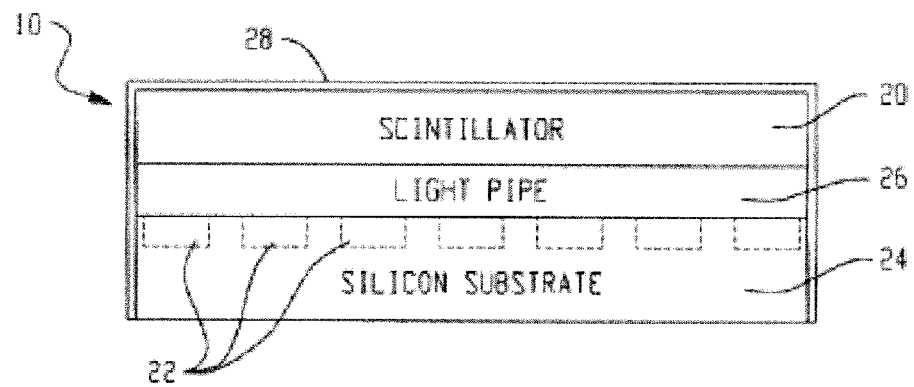
FIG. 2 diagrammatically shows a cross-sectional view of one of the pixelated digital radiation detectors of the TOF-PET system of FIG. 1.

With continuing reference to FIG. 1 and with further reference to FIG. 2, each radiation detector 10 includes a scintillator 20 that produces a scintillation or burst of light when the gamma ray strikes the scintillator 20. The burst of light is received by an array of detector pixels 22 monolithically disposed on a silicon substrate 24. As will be described, the detector pixels 22 are digital detector pixels that output values including a digital representation of a count of photons (denoted "count" in FIG. 1) and a digital representation of a timestamp (denoted "timestamp" in FIG. 1) indicative of when the burst of light corresponding to the scintillation event was detected by the detector pixel 22. Moreover, the plurality of radiation detectors 10 outputs indexing information including, for example, a detector index (denoted "$n_{detector}$" in FIG. 1) indicating which of the radiation detectors 10 output the radiation detection event, and a detector pixel index (denoted "$k_{pixel}$" in FIG. 1) indicating which detector pixel or pixels of that radiation detector detected the burst of light corresponding to the radiation detection event. The scintillator 20 is selected to provide high stopping power for 511 keV gamma rays with rapid temporal decay of the scintillation burst. Some suitable scintillator materials are LSO, LYSO, MLS, LGSO, LaBr and mixtures thereof. It should be appreciated that other scintillator materials can also be used. Although FIG. 2 shows the scintillator 20 as a single crystal, an array crystals can instead be used. Additionally, an optional planar light guide 26 can be interposed between the scintillator 20 and the detector pixels 22 to improve transmission of photons of the scintillation light burst to the detector pixels 22. The scintillator 20 and optional light guide 26 are optionally encased in a reflective coating 28 which directs scintillation light toward the pixels 22.

With continuing reference to FIG. 1, the digital data concerning radiation detection events are processed by a pre-processor 30 that performs selected data processing. For example, if a scintillation event is detected by a plurality of detector pixels, then the pre-processor 30 can employ Anger logic or other processing to identify spatial coordinates r for each radiation detection event and to estimate an energy of the detected radiation particle. The resulting spatial and energy information for each radiation detection event is stored in an events buffer 32. In other embodiments, the scintillator layer is divided into scintillator tiles sized to correspond with the detector pixels, and each detector pixel is optically coupled with a single scintillator tile. For example, each scintillator tile may include a reflective coating similar to the reflective coating 28 to channel the scintillation photons to the coupled pixel.

A gamma ray pair detection circuitry 34 processes the radiation detection events to identify pairs of substantially simultaneous gamma ray detections belonging to corresponding electron-positron annihilation events. This processing can include, for example, energy windowing (that is, discarding radiation detection events outside of a selected energy filtering window disposed about 511 keV) and coincidence-detecting circuitry (that is, discarding radiation detection event pairs temporally separated from each other by greater than a selected time filtering interval).

When a gamma ray pair is identified, a line-of-response (LOR) processor 38 processes the spatial information pertaining to the two gamma ray detection events (for example, with the two events represented by spatial coordinates $r_1$ and $r_2$, respectively, as computed by the pre-processing 30) to identify a spatial line of response (LOR) connecting the two gamma ray detections. Since the two gamma rays emitted by a positron-electron annihilation event are oppositely spatially directed, the electron-positron annihilation event is known to have occurred somewhere on the LOR.

In TOF-PET, the radiation detectors 10 have sufficiently high temporal resolution to detect a time-of-flight difference between the two "substantially simultaneous" gamma ray detections. A time-of-flight processor 40 analyzes the time difference between the times (denoted "$t_1$" and "$t_2$" in FIG. 1) of the two gamma ray detection events to localize the positron-electron annihilation event along the LOR. The result, accumulated for a large number of positron-electron annihilation events, is a set of histoprojections 42. A reconstruction processor 44 reconstructs the set of histoprojections 42 into a reconstructed image using any suitable reconstruction algorithm, such as filtered backprojection or iterative backprojection with correction. The resulting reconstructed image is stored in an images memory 46, and can be displayed on a user interface 48, printed, stored, communicated over an intranet or the Internet, or otherwise used. In the illustrated embodiment, the user interface 48 also enables a radiologist or other user to control the TOF-PET scanner 8; in other embodiments, a separate controller or control computer may be provided.

Figure 3:
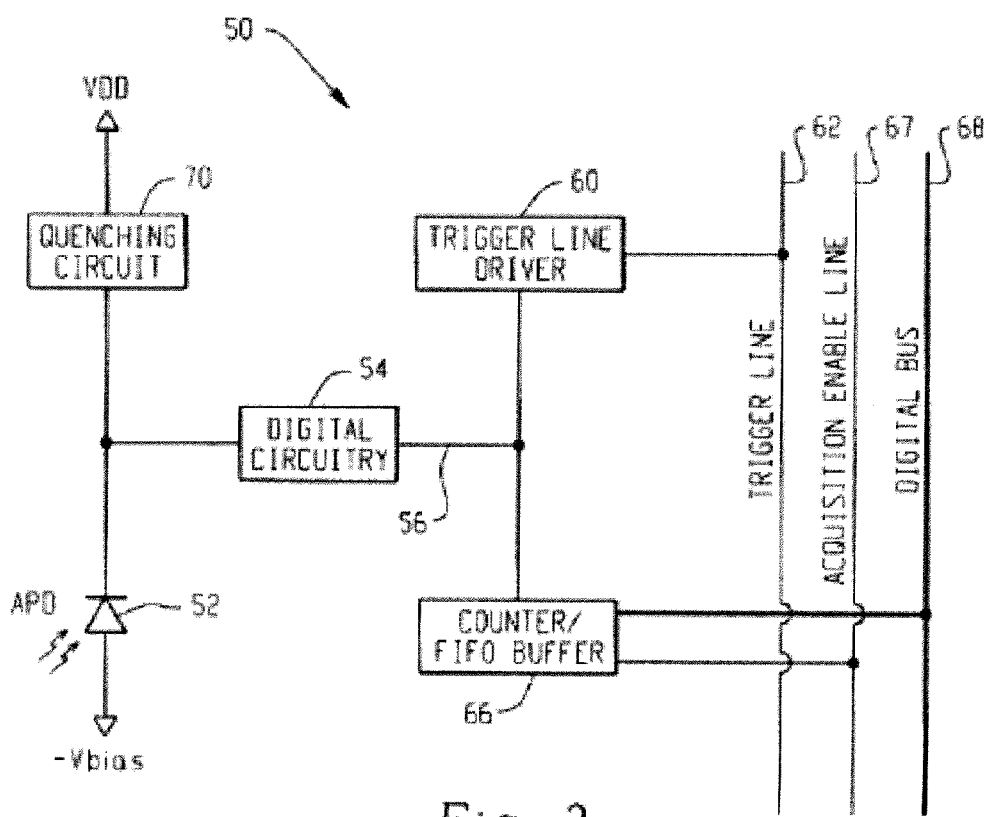
FIG. 3 shows a general circuit diagram of one of the detector cells of the pixelated digital radiation detector.

With reference to FIG. 3, each pixel 22 of the radiation detector 10 includes an array of detector cells 50; FIG. 3 shows a general circuit diagram of one such detector cell 50. A photodiode 52 is biased in a breakdown region and serves as an input to digitizing circuitry 54. An output 56 of the digitizing circuitry 54 has a first digital value corresponding to a quiescent state, and transitions to a second digital value responsive to detection of a photon by the photodiode 52. When the first photon of a scintillation burst is detected, the switching of the output 56 from the first digital value to the second digital value activates an open collector trigger line driver 60 which causes a trigger signal to be applied to a common trigger line or bus 62. The trigger signal in turn initiates a photon counter/FIFO buffer 66 (where FIFO="first in, first out") that counts the switchings of the digitizing circuitry 54 from the first digital value to the second digital value over an integration time period started by the trigger signal. In some other embodiments, an acquisition enable line 67 initiates the photon counter 66. A quenching circuit 70, which may be either active or passive, limits current through the photodiode 52 and is configured to facilitate transition the biasing circuitry from the second digital value back to the first digital value. Thus, the detector cell 50 may count more than one photon if the detector cell 50 is quenched back to the quiescent first digital value before the integration time period expires. The final count stored in the photon counter/FIFO buffer 66 is accessible via a digital bus 68.

The photodiode 52 is suitably biased in a Geiger-mode type of operation. When the photodiode 52 breaks down, large amount of charge (for example, about $10^6$ electrons per received detection in some photodiodes) is generated through the avalanche breakdown process. This charge is transported primarily through the quenching circuit 70, which has an effective resistance of typically several hundred kilo-ohms to limit the current flowing through the photodiode 52. With the current thus limited, charge remaining in the photodiode 52 distributes spatially to reduce the electric field in the avalanche region of the photodiode 52. This screening quenches the avalanche process and causes remaining carriers to be transported by drift out of the avalanche/depletion zone, causing recovery of the photodiode 52. Typically, the photodiode 52 includes a guard ring (not shown) around the periphery that prevents avalanche breakdown at the edges of the photodiode 52. The guard ring structure suitably acts like an ordinary reverse-biased PN diode with internal fields too low for the avalanche breakdown to occur.

Figure 4A:
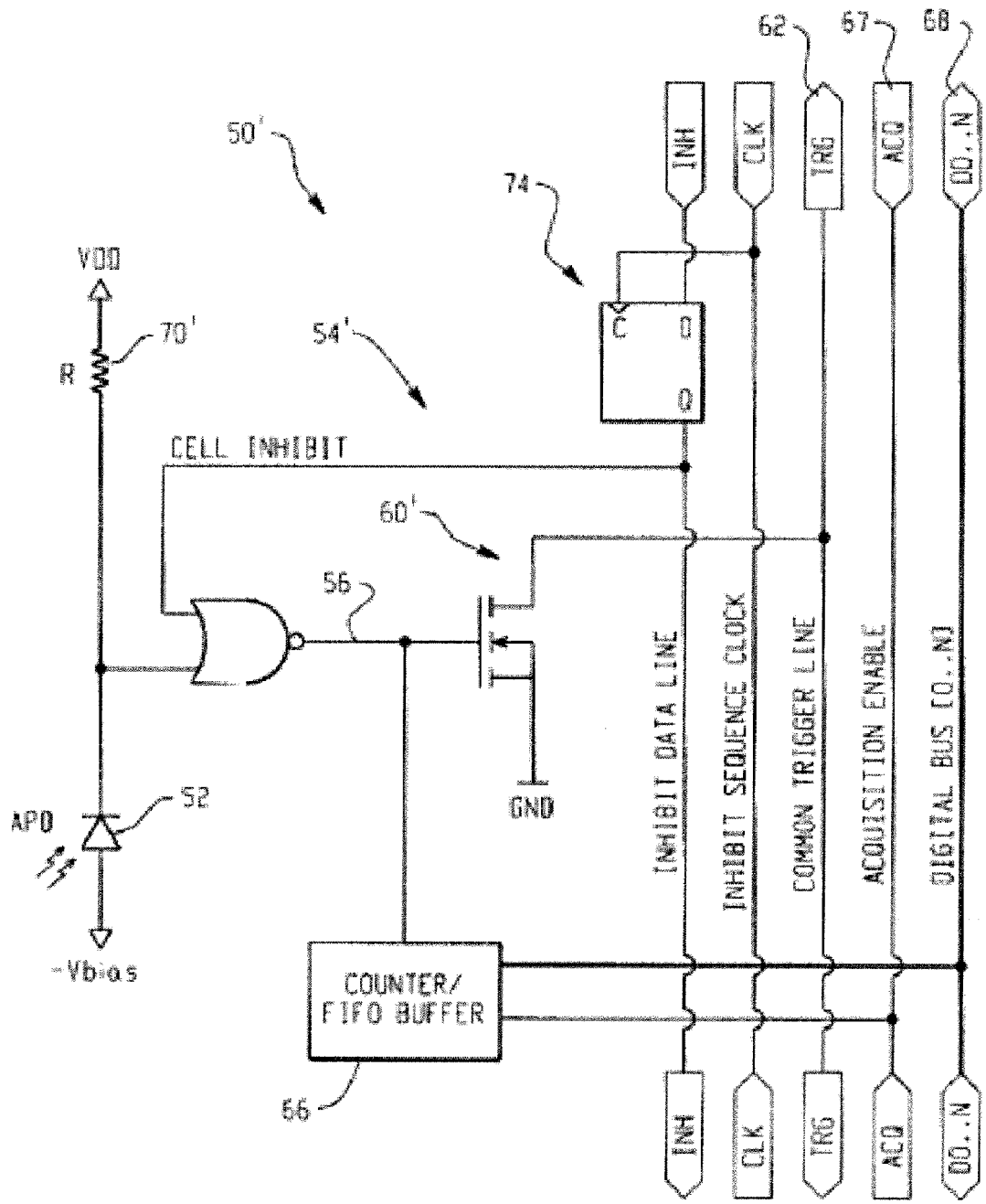
FIG. 4A shows a more detailed circuit diagram of one embodiment of one of the detector cells.

With reference to FIG. 4A, a more detailed circuit diagram of one example embodiment detector cell 50' is described. This embodiment includes a passive quenching circuit 70' embodied as a quenching resistor. On photon detection, the junction of the photodiode 52 breaks down and an electric current starts to flow through the photodiode 52 and the quenching resistor 70'. This current causes a voltage drop across the resistor 70', thus lowering the potential on the inverter input. The voltage difference relative to $V_{DD}$ should be large enough to drive the inverter output into a "high" state. The switching characteristics of the inverter can be optimized by adjusting the transistor widths. The inverter output returns to a "low" state automatically when the photodiode 52 recovers from the breakdown.

With continuing reference to FIG. 4A, the detector cell 50' further implements inhibit logic 74 which does not switch off a faulty detector cell completely, but rather prevents faulty detector cells from generating false triggers. Faulty detector cells will generate excess currents which are taken into account in the trigger validation circuit (described later). When using the detector cells 50', the trigger line 62 is tied to a "high" level via a pull-up resistor (not shown in FIG. 4A). This way, the triggers from all the detector cells 50' are logically "or"-ed together and the trigger line 62 is pulled down by that detector cell which detects the first photon.

Figure 4B:
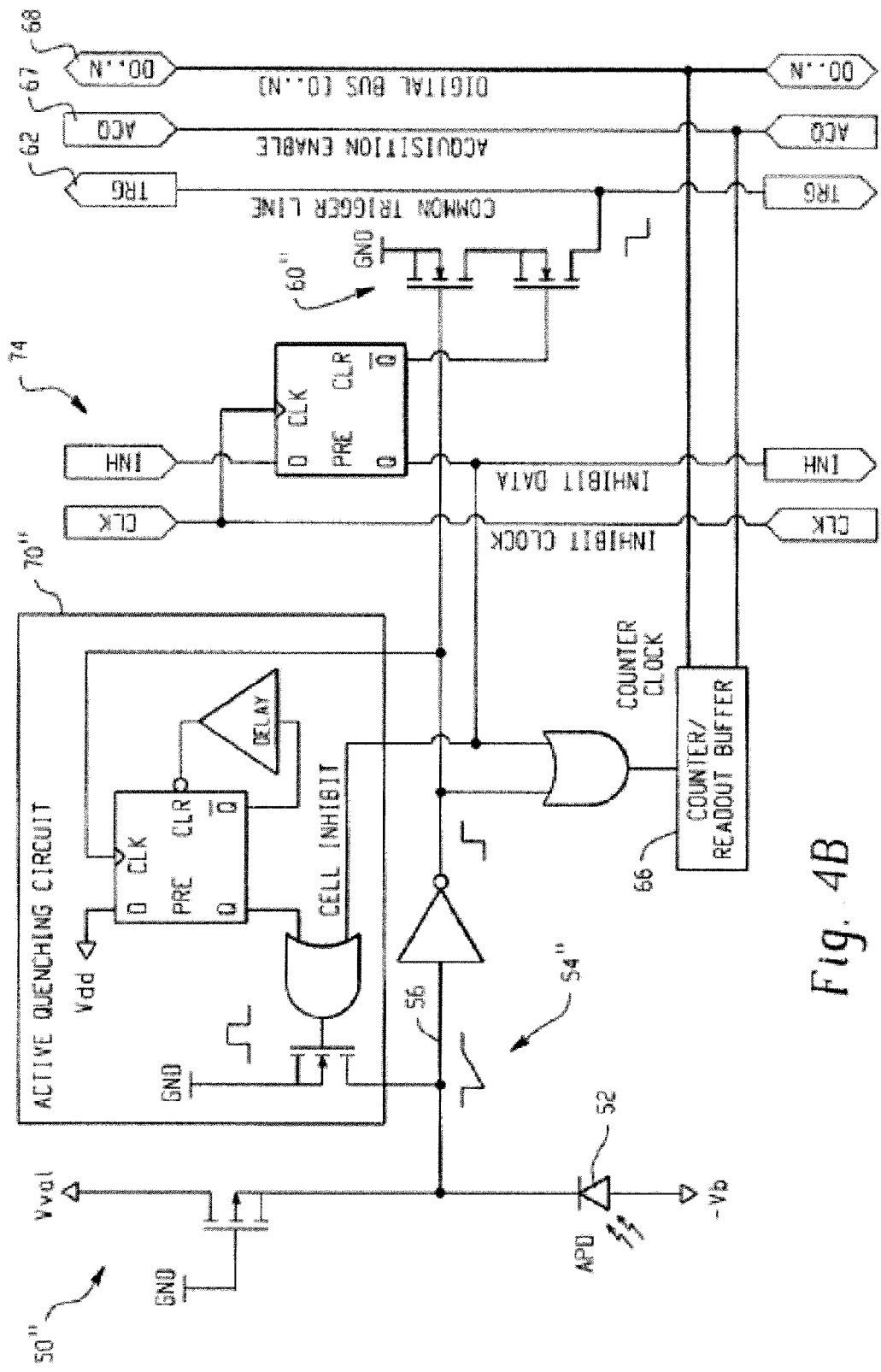
FIG. 4B shows a more detailed circuit diagram of another embodiment of one of the detector cells.

With reference to FIG. 4B, a more detailed circuit diagram of another example embodiment detector cell 50" is described, which includes an active quenching circuit 70" to speed up the discharge of the junction capacitance of the photodiode 52 to return to the quiescent level, thus reducing the recovery time of the photodiode 52. Shorter recovery times are expected to lead to higher sensitivity, since a given detector cell 50" is more likely to count more than one photon during the integration time period when it recovers quickly, and are expected to lead to higher dynamic range and better energy resolution of the detector cell 50". The photon counter 66 is enabled either by the trigger line 62 or a dedicated line if a hierarchical trigger network is used, which is pulled down by that detector cell which detects the first photon, and is held down by main pixel logic (not shown in FIG. 4B) for the integration time period. The number of detected photons accumulated by the photon counter 66 is transferred from the photon counter 66 to a buffer or other digital storage (not shown in FIG. 4B) on the rising edge of the trigger line 62 or a dedicated readout line. Subsequently, the counter 66 is reset automatically, for example by the low level of the inverted and delayed signal on the trigger line 62, in preparation for the next scintillation burst detection event. In this arrangement, the dead time between integration time periods can be as low as the buffer transfer time plus the reset time of the counter 66, which in some embodiments is expected to be less than one nanosecond for CMOS implementations. The detector cell 50" of FIG. 4B also includes inhibit logic 74 to prevent false triggers from faulty detector cells.

Figure 5:
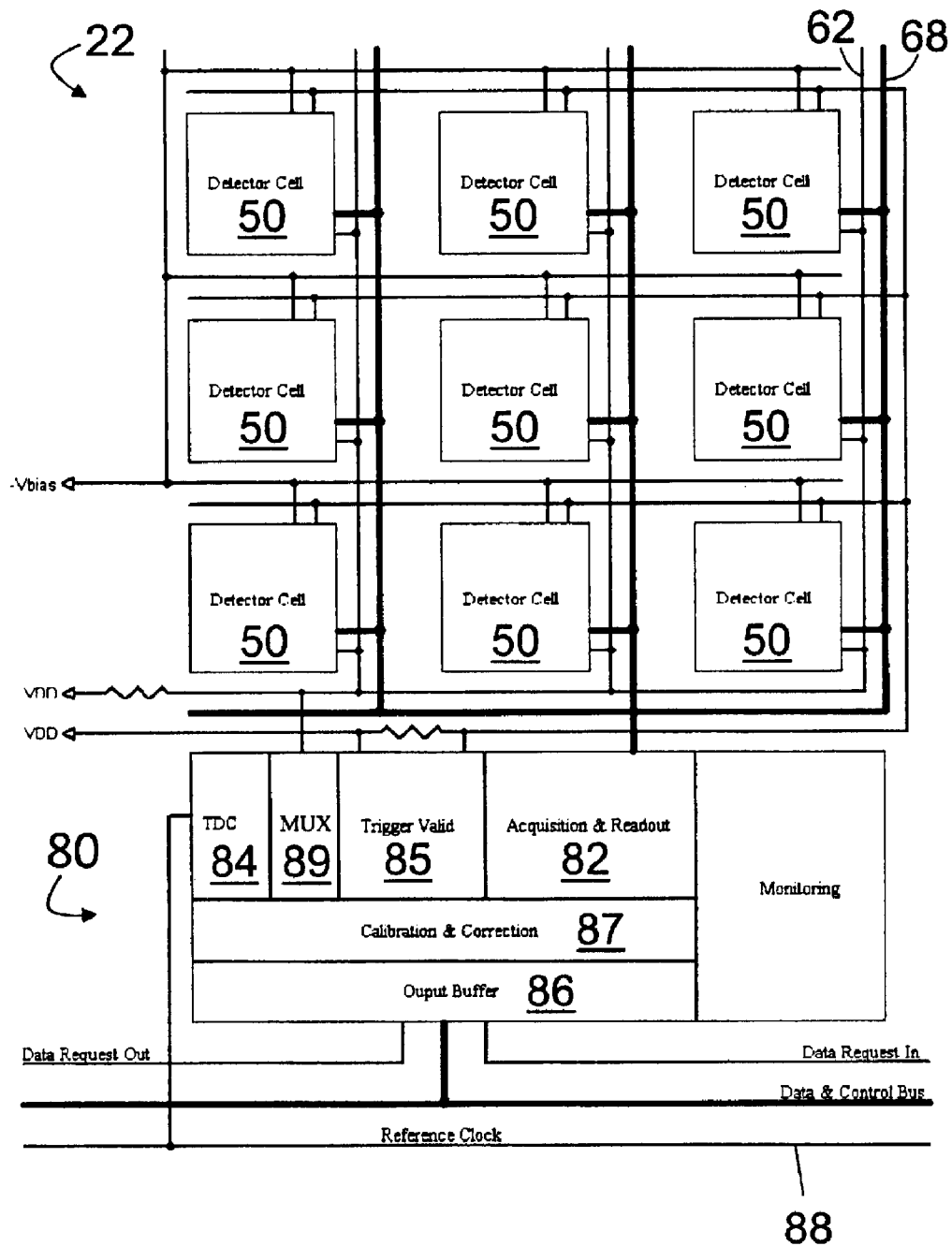
FIG. 5 shows a circuit diagram of one pixel of the pixelated digital radiation detector.

With reference to FIG. 5, each pixel 22 of the radiation detector 10 includes a two-dimensional array of detector cells 50 and associated pixel-level digital pixel logic 80. Digital readout circuitry for the pixel 22 includes pixel-level digital acquisition and readout circuitry 82 and associated circuitry at the detector cell level.

With reference to FIGS. 3 and 5, the digitizing circuitry 54 of each detector cell 50 provides a threshold-based binary digital output indicating whether or not the photodiode 52 of that detector cells has entered breakdown. The digital circuitry 54 outputs a first binary value when the photodiode 52 is in its quiescent state, and transitions to a second binary value when the photodiode current increases beyond a threshold value indicative of photon detection. The signal of each photodiode 52 is thus digitized at the level of the detector cell 50. Readout is performed by the pixel-level logic counting the digital transitions of the detector cells to produce a digital pixel output indicative of the number of detected photons. Compared with the summing of analog photodiode currents to generate an analog pixel output as is done in analog SiPMs, the digitize-and-count method of FIGS. 3 and 5 is far less sensitive to bias variations, operating temperature variations, tolerances in components of the quenching circuit 70, or so forth. As long as these secondary effects do not cause erroneous switching or missed switching of the thresholding digital circuitry 54, they generally do not affect the energy resolution of the detector cell 50.

In some readout approaches, the detector cells 50 are addressed like in a standard memory block, using address decoders for the rows and columns of the array of detector cells 50. This solution provides a sequential readout of the cell data, in which case the pixel-level readout circuitry 82 can be a simple digital accumulator. In other readout approaches, cells lines are read out in parallel, with each line having its own accumulator for the partial sum, and the partial sums are added in a parallel adder tree. In yet other readout approaches, the adders are incorporated into the detection cells, so that the sum of the whole line is obtained while clocking the data out and the line sum is read out from the last detector cell in the line. As the summation in this latter readout approach can be pipelined, the readout architecture is fast, allowing short readout intervals.

If the detector cell-level photon counters 66 or counters of the pixel-level readout circuitry 82 are likely to saturate, then the counters should not be allowed to wrap around. For example, a four-bit counter counting from 0 . . . 15 should not be allowed to increment from 15 back to 0. By avoiding wrap-around, saturation of the pixel 22 can be detected when the counter reads its highest value (e.g., 15 for a four-bit counter). The number of bits for avoiding wrap-around depends solely on the minimum anticipated cell recovery time and the maximum length of the integration period. While the integration window is a design parameter, the cell recovery time is of a statistical nature, as photon detection probability is a function of the slowly rising over-voltage during cell recovery. In an actively quenched cell however, a minimum recovery time is defined by the monoflop delay. Thus, in this case, it is possible to design the counter wide enough to avoid overflow. The digital bus 68 can be either a parallel or a serial bus, depending on space and time constraints.

With continuing reference to FIG. 5, the digital pixel logic 80 further includes trigger digital circuitry 84, trigger validation circuitry 85, and an output buffer 86 that stores the photon count of the pixel 22. The trigger digital circuitry 84 accesses a reference clock 88 (shown as an electrical trace that is connected to a suitable oscillator or other clocking device not shown in FIG. 5) to provide a time reference for the trigger digital circuitry 84. The trigger digital circuitry 84 determines the time stamp of a radiation detection event in a global (for example, scanner) time frame. The trigger digital circuitry modules 84 of all the pixels 22 of the scanner run synchronously at a precision of preferably less than 100 ps. The reference signal 88 is used to synchronize the trigger digital circuitry modules 84 of the pixels, providing them with a common time base for the entire scanner. In some embodiments, the integration time period is a fixed time interval starting at the occurrence of the trigger signal. In other embodiments, the integration time period is dynamically terminated when the rate of new counts decreases below a threshold value.

The trigger digital circuitry 84 is also preferably configured to output the digital timestamp (see FIG. 1) associated with the count. The digital timestamp is based on a time of the trigger signal output by the trigger line driver 60 of the first one of the detector cells 50 that detects a photon from a scintillation burst. The pixel logic 80 optionally still further includes data correction registers and inhibit sequence drivers. Automated test and calibration circuitry 87 is also optionally implemented by the pixel logic 80. In one test/calibration method, the dark count rate of the pixel 22 (possibly including background counts produced by intrinsic radioactivity of the scintillator 20) is monitored. In another test/calibration method, an external excitation from a test charge injected into the detector cells 50 is used to test and calibrate the pixel 22.

With continuing reference to FIG. 5, it will be appreciated that due to dark currents, crosstalk, thermal excitations, or so forth, it is possible that one of the detector cells 50 may produce an inadvertent trigger signal starting an integration time period. The trigger validation circuitry 85 validates the trigger signal and aborts the integration if it is determined that the trigger signal was false. In one approach, the trigger validation circuitry 85 analyzes the current flowing through the bias network of the pixel 22. If the total current stays below a certain current threshold for a selected time interval (e.g. for 10 nanoseconds into the acquisition time period) as measured by a discriminator or other circuitry, then the acquisition is aborted and an automatic reset sequence is initiated in preparation for the next trigger. If the current exceeds the current threshold, the discriminator output will rise to a 'high' level and the acquisition will continue. In some embodiments, rather than using a fixed integration time period, the falling edge of the bias current discriminator is used to detect the end of the scintillation burst so as to adapt the integration time period to substantially match the end of the acquisition interval. This can suppress pile-up in high count rate applications. Another suitable method makes use of the fact that the probability of two thermally generated triggers inside a short time window decreases with the distance of the triggering cells since thermal triggers are generally not correlated. In contrast, the scintillation burst should act on detector cells 50 across the light-sensitive area of the pixel 22. Thus, the trigger validation circuitry 85 can analyze the triggers from individual detector cells 50, for example, and validate the trigger signal if two distant lines generate a trigger signal within a selected time window. Other approaches for trigger validation can also be used, such as employing a current sensor with adjustable discriminator set at a trigger threshold higher than the single photon level.

In some other embodiments, the counter 66 is triggered by the acquisition enable line 67. Triggering on the first photon can be problematic if there is a high background flux of photons unrelated to positron-electron annihilation events. This background can be the result of, for example, a secondary slow decay mode of the scintillator. In such cases, detector cells fire frequently, increasing the dead time of the pixel. To provide more robust counter initiating, at the detector cell level (FIG. 3, 4A, or 4B) the photon counter is enabled by the separate, 'acquisition enable' line 67 which is pulled down by the pixel logic on either the detection of the first photon (trigger line goes down) or by the discriminator of the trigger validation circuit 85 when the current through the bias network has exceeded the user-defined trigger level. This line defines the length of the integration window and is driven by the pixel logic. At the detector pixel level (FIG. 5), the trigger validation circuit 85 is extended to include a multiplexer 89 selecting either the trigger line 62 (for a single photon trigger) or the leading edge discriminator output (for multiple photon trigger) as the input to the time to digital converter/trigger validation circuits. The trigger validation circuit 85 is extended to provide the 'acquisition enable' signal 67 to the detector cells 50, 50', 50".

Alternatively, if triggering at single-photon level is not required, a suitable logic can be implemented to generate the trigger signal if a selected number of cells (trigger lines) become active at the same time. This implementation has the practical advantage requiring only digital components. However, in this case, the threshold is defined only statistically. In some other embodiments, the open collector driver is optionally omitted from the detector cells and a modified design is used in the trigger validation circuit.

Figure 6:
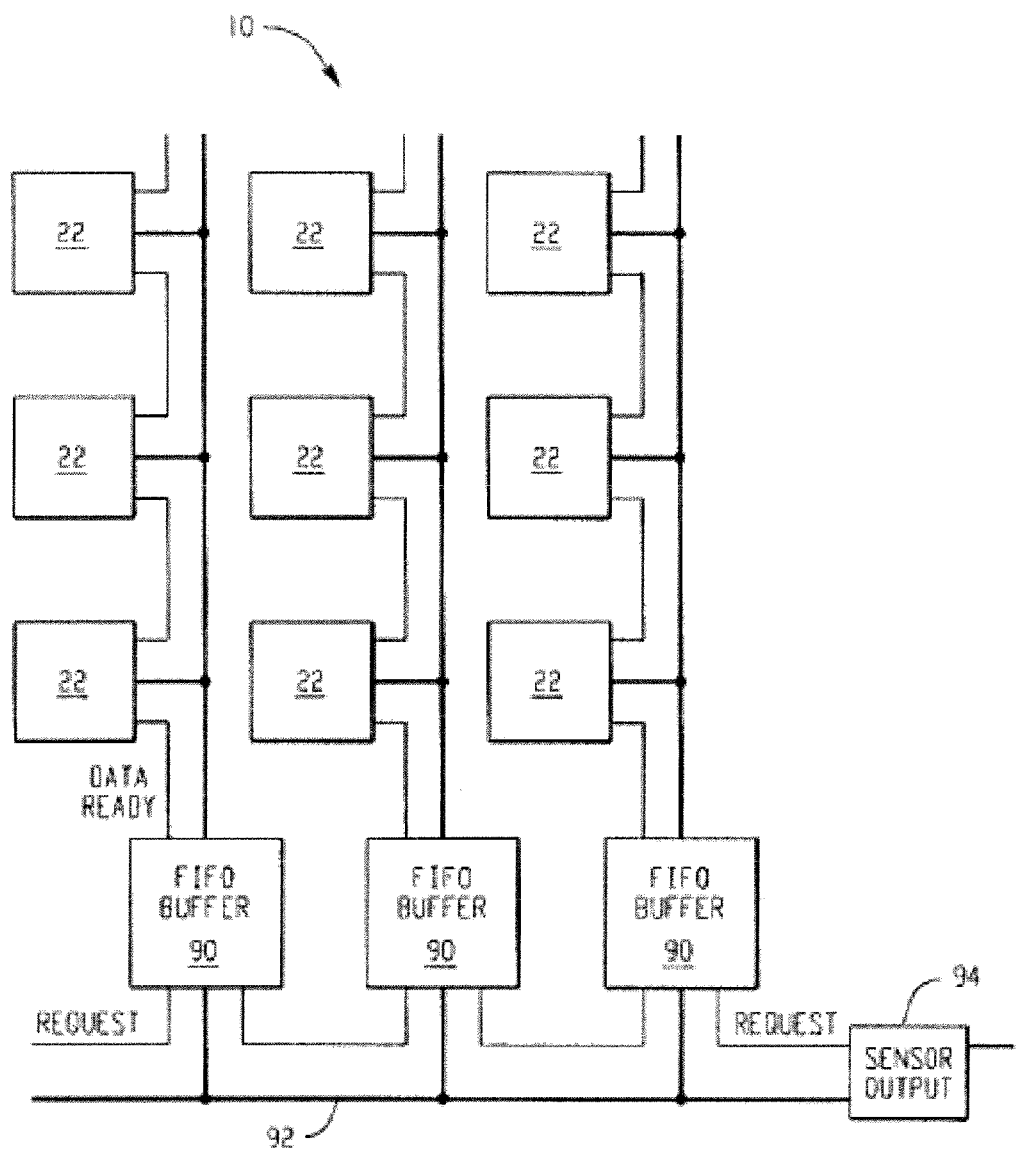
FIG. 6 shows a circuit diagram of one the pixelated digital radiation detectors.

With continuing reference to FIG. 5 and with further reference to FIG. 6, the pixels 22 are arranged in a two-dimensional array to define the light-sensitive surface of the pixelated radiation detector 10. The embodiment shown in FIG. 6 uses a pixel readout in which each line of pixels 22 is read out by FIFO buffers 90. The output buffers 90 each include tristate output buffers allowing the data to be transferred over a shared digital data bus 92. Optionally, the events are sorted according to their time stamps by the readout arbitration in the line output buffers 90 and also by the shared bus arbitration by shared digital data bus 92, thus leading to a stream of event data which is sorted over time. This optional feature substantially simplifies the search for coincident events. A data request daisy-chain is suitably used for write access arbitration. The daisy-chained sums are transferred to a radiation detector output buffer 94 for transfer off-chip.

Figure 7:
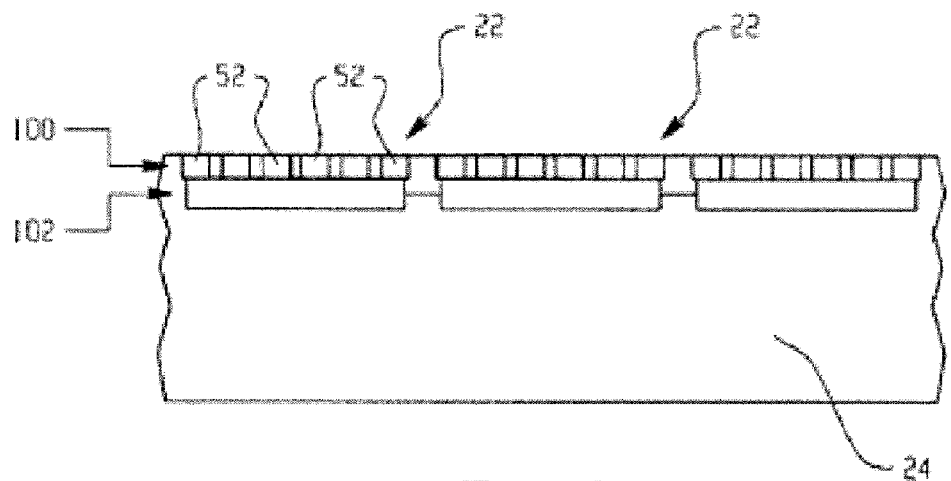
FIG. 7 shows a cross-sectional view of one physical layout embodiment of the pixelated digital radiation detector, in which the photodiodes define a photodiode layer and the digital circuitry is disposed in a digital circuitry layer separate from and electrically coupled with the photodiode layer.
Figure 8:
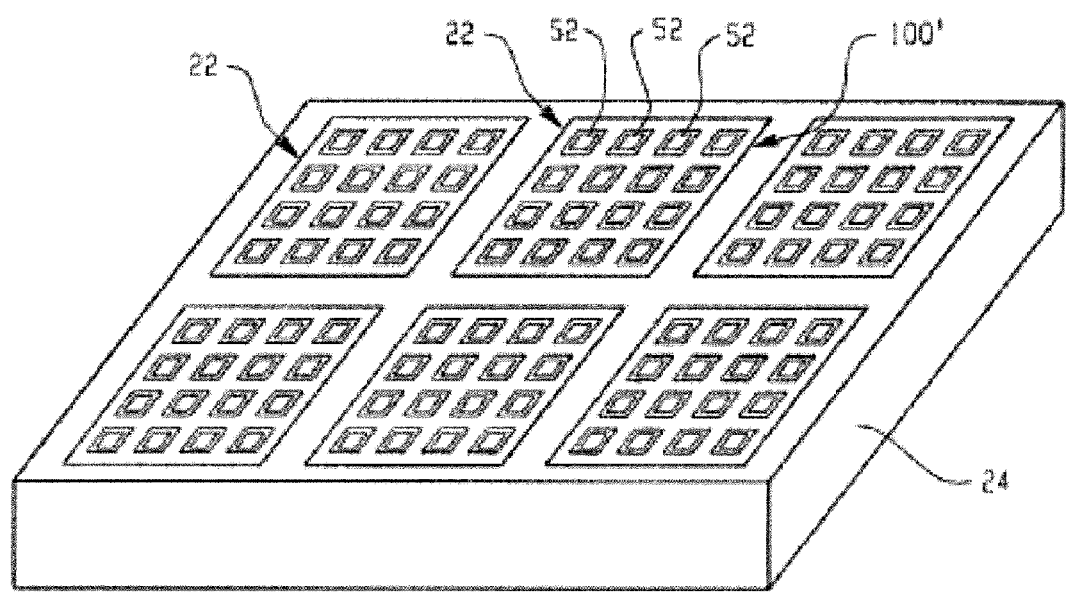
FIG. 8 shows a perspective view of another physical layout embodiment of the pixelated digital radiation detector, in which the photodiodes define a photodiode layer and the digital circuitry is disposed in the photodiode layer interspersed amongst the photodiodes.

With reference to FIGS. 7 and 8, in some embodiments the digital circuitry (such as the digital biasing circuitry 54, 54', 54", digital triggering circuitry 60, 60', 60", 84, and readout digital circuitry 66, 82) of the radiation detector 10 are defined by CMOS circuitry disposed on the silicon substrate 24. Various physical layouts can be used. In a vertically segregated layout shown in FIG. 7, the photodiodes 52 of the array of detector cells 50, 50', 50" define a photodiode layer 100, and the digital circuitry are disposed in a CMOS digital circuitry layer 102 separate from and electrically coupled with the photodiode layer 100. In an alternative layout shown in FIG. 8, the photodiodes 52 define a photodiode layer 100', and the CMOS digital circuitry (such as the digital biasing circuitry 54, 54', 54", digital triggering circuitry 60, 60', 60",

84, and readout digital circuitry 66, 82) are disposed in the photodiode layer 100' interspersed amongst the photodiodes 52.

Because CMOS logic draws power only when switching states, only those parts of the radiation detector 10 that are continuously actively clocked by the clock 88 will contribute to the baseline power consumption. Since the pixel 22 is activated by a trigger signal generated by one of the photodiodes 52 which are biased in the breakdown region in the quiescent state, power consumption is dependent on the photon detection rate and, thus, on the flux of received photons plus the dark count rate. Control of power consumption of the pixel 22 can be implemented by deliberately increasing the dead time of an individual pixel between two acquisitions. This could be done automatically by the pixel logic 80 depending on the temperature of the pixel. The temperature of the pixel can be measured directly by a temperature sensor (not shown) or estimated indirectly from the dark count rate of the pixel 22.

Since CMOS logic draws power only when switching states, the overall power consumption can be dramatically reduced by using a CMOS implementation over an analog implementation. For example, in some embodiments of an analog implementation, the power consumption per channel is 30 mW and the global part of the chip is 162 mW. For a more practical implementation, such as on a clinical apparatus with 28,336 channels or 1890 chips, the power consumption would be a constant 1156 W. On the other hand, the power consumption for a CMOS implementation, such as the various implementations described herein, has two different values, a static value and a dynamic value. The static power consumption is the power required when there are no counts and hence no switching of states. It does include power for the logic of for the dynamic switching as the logic must be ready to receive counts. The dynamic power consumption is the power required when the detector is actively receiving counts, and hence switching states. The power consumption in active state is dependent on the amount of activity; the more counts and switching of states, the power that is required. The static power consumption for a similar 1890 chip detector is about 10 W or less. The dynamic power consumption can vary, depending on the activity, but is typically about 300 W or less.

A problem can arise if the scintillation burst of light produces a flux of photons that is high enough to cause substantially all of the detector cells 50, 50', 50" of one or more of the pixels 22 to transition from the first digital state to the second digital state during the integration time period. In this case, the pixel 22 saturates, and the actual intensity (that is, the flux of photons) is not accurately measured. This saturation problem can be addressed in various ways.

In one approach, the photosensitive area defined by the photodiodes 52 is broken into a larger number of smaller photodiodes. The reduced area of each photodiode reduces the likelihood that it will detect a photon. The larger total number of photodiodes provides higher pixel-level sensitivity to the flux of photons, although it generally does not fully compensate for the reduced area of each cell. The detector cells should have some separation to reduce optical crosstalk between neighboring detector cells. Typically, the separation of the cells is in the order of several microns or less, when trenches filled with opaque material are used for the separation. Thus, increasing the number of cells generally reduces the ratio of sensitive area to the total area of the cell to some degree. Additionally, increasing the number of detector cells, while keeping the cell size constant, typically leads to a proportional increase of the dark count rate.

Figure 9:
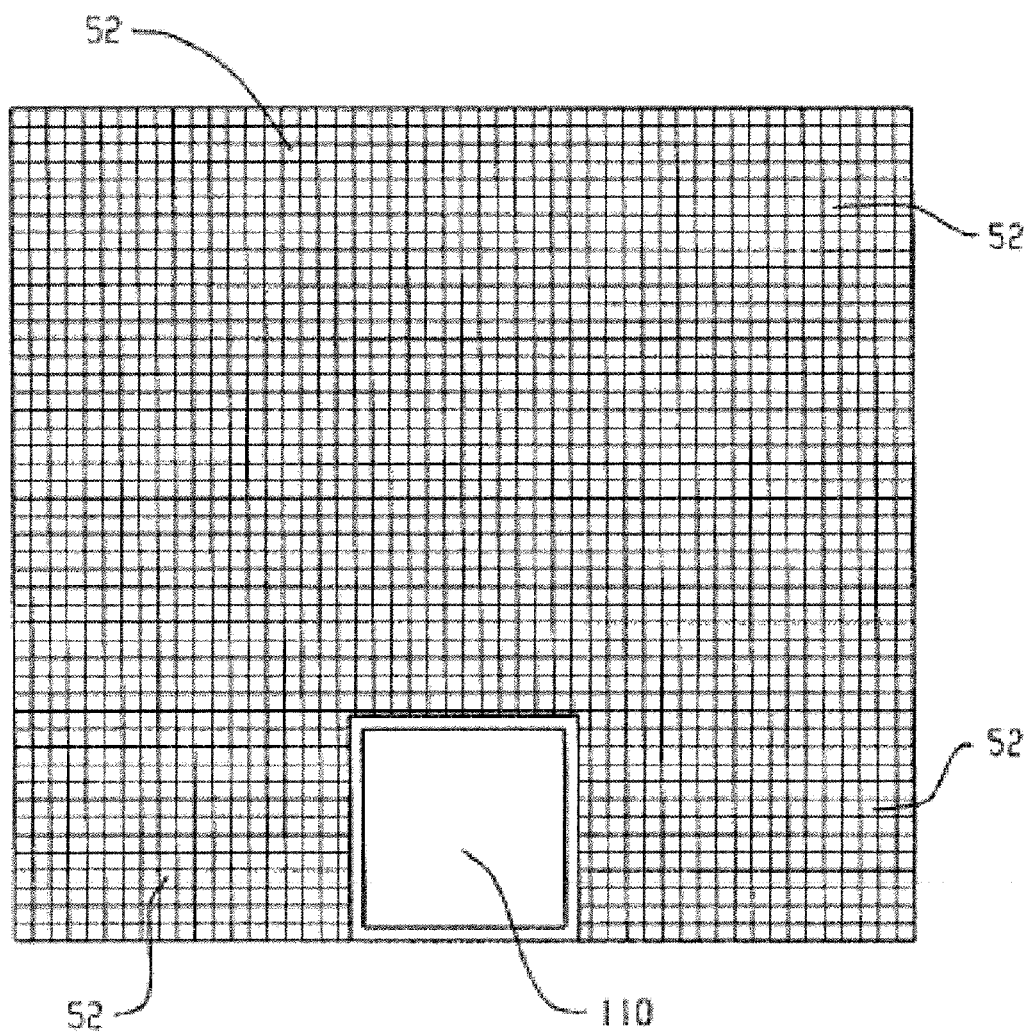
FIG. 9 shows a plan view of the light-sensitive area of a variant device which includes the pixelated digital radiation detector area and an additional proportional photodiode that produces an analog photocurrent when the flux of photons is high enough to saturate the pixelated digital radiation detector area.

With reference to FIG. 9, in another approach for addressing the saturation problem, a proportional photodiode 110 is included in the photosensitive area. The proportional photodiode 110 is larger than the photodiodes 52 used in digital detection. The proportional photodiode 110 is configured to produce an analog photocurrent proportional to the flux of photons impinging upon the pixel 22 when said flux of photons is high enough to cause substantially all of the detector cells 50, 50', 50" of the pixel 22 to transition from the first digital state to the second digital state during the integration time period. Although shown along one side of the array of pixels 22 for simplicity of fabrication, the proportional photodiode 110 can be located in other positions respective to the array, such as centered in the array or at a corner of the array. Moreover, in some embodiments the proportional photodiode 110 may be distributed as a plurality of smaller electrically interconnected proportional photodiodes, such as a proportional photodiode located at each corner of the array of pixels 22. In the variation of FIG. 9, the trigger signal output by the first one of the photodiodes 52 to detect a photon is still suitably used to provide the timing information for the gamma ray detection event. Thus, the timestamp output by the radiation detector 10 is used; however, if the digital photodiodes 52 saturate, then the photocurrent produced by the proportional photodiode 110 is used to indicate photon flux intensity rather than using the digital count. The proportional photodiode 110 can be a conventional PIN diode, an avalanche photodiode with integrated analog or digital readout circuitry, or the like.

The pixelated digital radiation detectors are described herein in conjunction with an example TOF-PET application. However, the skilled artisan can readily adapt the disclosed pixelated digital radiation detectors for other application, such as single-photon emission computed tomography (SPECT) imaging, transmission computed tomography (CT) imaging, astronomy applications, and so forth. For radiation detection applications in which the photodiodes 52 are directly sensitive to the radiation, the scintillator 20 is suitably omitted from the radiation detector 10.

One skilled in the art should understand that while most of the embodiments have been described in conjunction with digital circuitry, portions of the invention can be implemented in conjunction with analog circuitry. For example, the following description provides a method of disabling defective cells in an analog circuitry system. Such embodiments are incorporated within the scope of this disclosure.

A defective cell disabling method for an analog circuit system can comprise of two separate stages, namely a sensing stage and a calibration stage. During the sensing stage, a SiPM array or device under test (DUT) is biased at the nominal bias voltage above threshold in a light-tight setup. The Geiger-discharge in semiconductors generates secondary light photons, approximately 3 per 100,000 electrons in the junction on average. Thus, a cell with gain 1,000,000 will generate about 30 optical photons. The average wavelength of these photons is about 1 μm, thereby enabling the photons to travel large distances in silicon before being absorbed. Some of these photons trigger breakdowns in neighboring cells, commonly referred to as optical crosstalk, if proper shielding is not used. Other photons can escape the silicon and can be detected by appropriate single photon detectors. The sensing detectors must be 1:1 coupled to the DUT cells. Thus, the trigger rate of the sensing detectors can then be directly associated with the dark count rate of individual cells. Additional measurement of the charge pulse of the DUT can be used to directly measure the gain and its variation for individual DUT cells. However to collect sufficient statistics, such measurement would likely mean a significant increase of the measurement time.

Based on the data acquired in the sensing stage, a laser beam will disable faulty cells. Additionally, the number of active cells per pixel can be adjusted to equalize the dynamic range of the pixels, if required. In some implementations, a fuse is used to disable the faulty cells. While a fuse would undesirably consume additional area, this can be minimized if the fuse is placed over the guard ring. Another alternative would be to cut the poly resistor itself.

Figure 10:
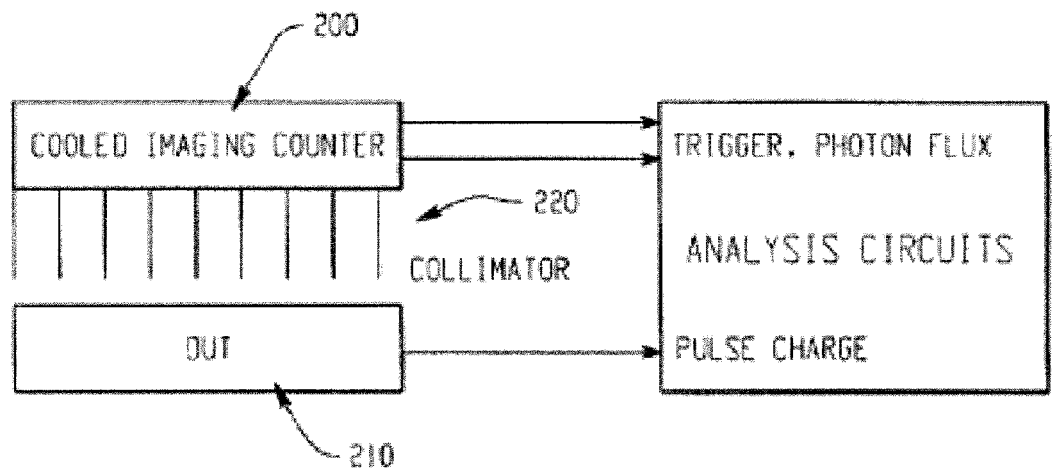
FIG. 10 shows an illustrative example of the measurement setup used in the first stage of a defective cell disablement process for detectors including analog circuitry.
Figure 11:
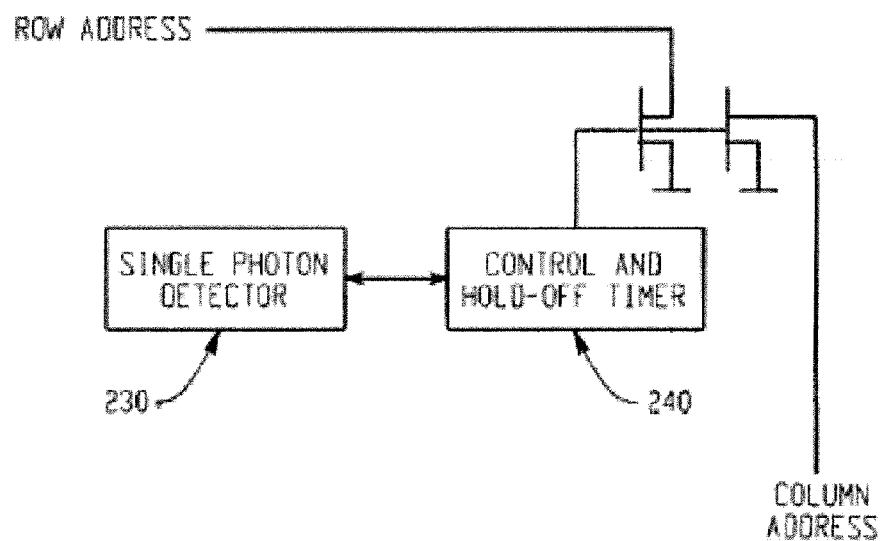
FIG. 11 shows a block schematic of one imaging counter cell.
Figure 12:
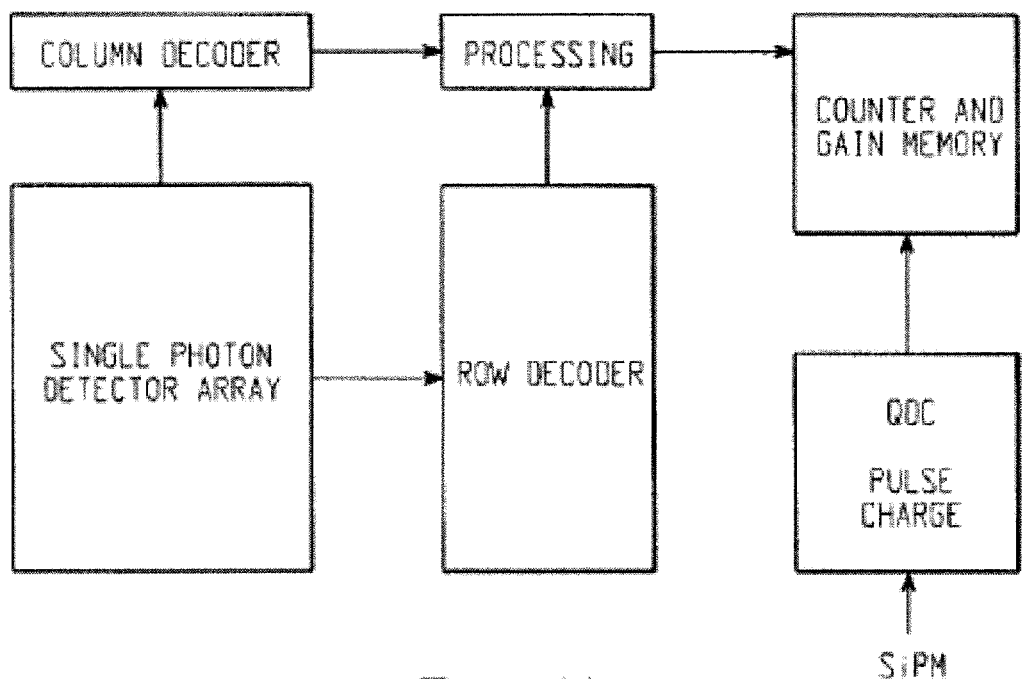
FIG. 12 shows a sensor block diagram.

An illustrative example of the measurement setup used in the first stage is shown in FIG. 10. In FIG. 10, a single photon counter array 200 is 1:1 coupled to the DUT 210 using a collimator structure 220. One skilled in the art should understand that if the sensing detector has the same pixel size as the DUT, proximity coupling could be used to increase the sensitivity of the system. The single photon counter array 200 must have significantly lower dark count rate and thus has to be cooled down to at least −50° C. Each detector 230 in the photon counter array 200 is triggered by photons emitted by the Geiger-mode discharge. The detector indicates the event by pulling down the row and column lines and starting a hold-off interval to avoid double counting of the same event. The length of the hold-off interval must be adjusted to the recovery time of the DUT. An active quenching/recharge circuit 240 can be used to obtain well-defined hold-off intervals. Additional circuits can be used to measure the charge of the pulse in correlation to the coordinates of the event. A block schematic of one imaging counter cell is shown in FIG. 11, while a sensor block diagram is shown in FIG. 12.

Figure 13:
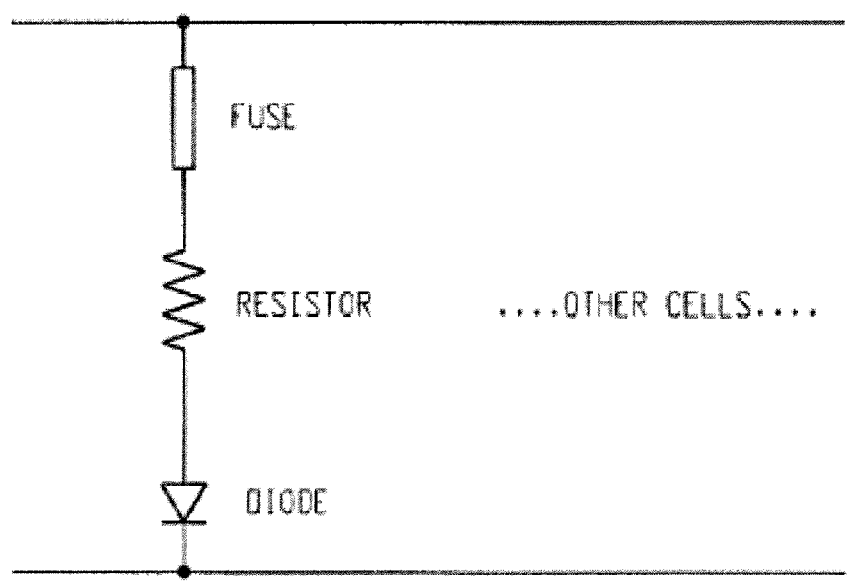
FIG. 13 shows a photodetector incorporating a fuse for disablement.

Increasing the DUT temperature can be used to accelerate the measurement. In the calibration stage, the pixel dark count rate and gain data is used to select a subset of cells that will be disabled. This can be any number of defective cells as well as other cells that can be disabled to provide uniformity. To achieve this, a laser is used to cut the fuses in these cells, as illustrated in the modified detector cell shown in FIG. 13.

Regardless of whether a digital or analog disablement process is used, a report can be generated allowing a user to determine how many cells were disabled because they were deemed faulty. The report can further provide the location of the disabled faulty cells. The location of the disabled faulty cells can, in some embodiments, be used to disable other cells. Typically this would be done in some sort of geometrical pattern to allow for more uniform detection of radiation about the detector. Furthermore, the disablement of other cells can be automatic, in response to manual input or feedback, or a combination thereof.

The resulting silicon photomultiplier array will have lower dark count rate at the expense of decreased sensitivity because of the area lost due to dead cells. The loss in dynamic range can be accounted for beforehand by integrating higher number of smaller-sized cells in the pixels. It should also be appreciated that the fuse implementation can be used in combination with digital circuitry. For example, the fuse can be used for calibration, while the digital circuitry is used for the count detection. Other embodiments incorporating these types of ideas are also contemplated by this disclosure.

In some embodiments in which a trigger at the single photon level is not needed, a leading edge discriminator can be used to generate the trigger signal and to suppress dark counts. In other embodiments the trigger signal can be generated digitally by applying a logical operation on the trigger lines. For example, a pixel can be subdivided into two halves, or blocks, and the trigger signal is only generated if both halves detect the photon. In such embodiments, the number and size of the blocks can be adjusted to set the average threshold and the selectivity. Of course, other similar designs can be implemented, including, but not limited to, other geometries and other ways of correlating pixel blocks.

As described herein, the use of digital SiPM detector arrays has certain advantages in PET, SPECT, and other radiological imaging techniques. However, existing radiation detector systems for PET, SPECT, and the like typically use analog detector arrays for detecting scintillation light, for example employing analog-output devices such as photomultiplier tube (PMT) devices. Retrofitting such a system with a digital SiPM detector is difficult or impossible because the digital SiPM has an output that is different in kind from the analog output of a PMT or other analog device.

Figure 14:
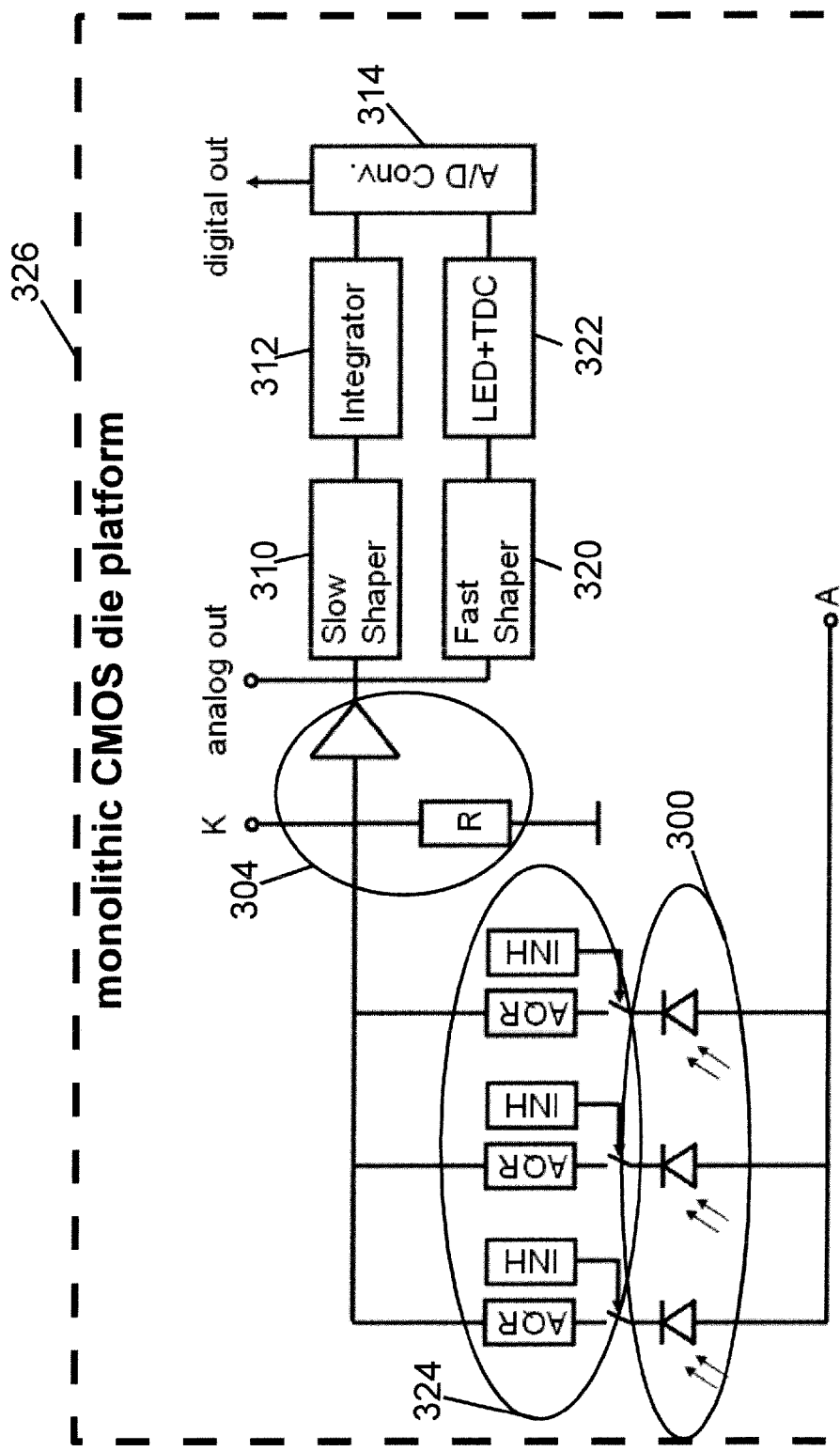
FIG. 14 shows a block schematic of a mixed-mode detector circuit providing either analog or digital output, fabricated monolithically on a CMOS die platform.

With reference to FIG. 14, a detector array is shown that provides selectable analog or digital output. An array of Geiger-mode avalanche photodiode (APD) devices 300 and either passive or active quenching and recharge circuits 324, are interconnected in parallel and are biased across anode and cathode terminals K, A. The skilled artisan will recognize this as a typical analog SiPM configuration, for which photon detections by the APD devices 300 cause discharge of the APD devices producing known amount of electrical charge that is dumped to the output terminals K, A. An "analog out" signal, again corresponding to an analog SiPM configuration, is taken from the output of a transimpedance amplifier 304. This output will exhibit a distinct current pulse of known magnitude and duration for each detected photon, corresponding to the known amount of electrical charge that is dumped to the output terminals K, A. The transimpedance amplifier 304 amplifies and outputs the analog signal with a defined impedance, thus simplifying external readout circuitry. The skilled artisan will recognize the biasing configuration using anode and cathode terminals K, A, and the readout configuration using the transimpedance amplifier 304 are conventional electrical connections for a PMT device or other analog detector such as is typically used for detecting scintillation light.

Thus, the components 300, 304 provide plug-in compatibility with existing PMT or other analog detector systems. The modifications for such a retrofit are limited to reconfiguration or adjustment of parameters such as the bias across the anode and cathode terminals K, A, gain parameters for processing the analog output, or so forth.

The detector array shown in FIG. 14 includes additional circuitry enabling digital operation to produce digital values of both the energy and timestamp. The energy digitization circuitry includes a slow shaper circuit 310 inputting into an integrator circuit 312, the output of which is digitized by analog-to-digital (A/D) conversion circuitry 314 to generate a digital representation of the pulse energy. The time digitization circuitry includes a fast shaper circuit 320 inputting into a leading-edge discriminator (LED)/time-to-digital conversion (TDC) circuit 322, the output of which is integrated by the A/D circuitry 314 with the digitized energy information to generate a "digital out" signal that provides both time and energy information. The digital operation circuitry further optionally includes inhibit logic 324 such as has already been described herein, that prevents faulty APD devices 300 from generating false triggers. The optional inhibit logic 324 is optionally also used in analog mode operation to switch faulty APD devices out of the parallel circuit so as to reduce dark current.

The digital mode operation of the detector array of FIG. 14 differs from the digital operation of digital SiPM devices disclosed elsewhere herein (such as with reference to FIGS. 4A and 4B) in that the APD devices 300 of FIG. 14 are interconnected in parallel and hence are not individually addressable. The number of APD devices 300 placed electrically in parallel is chosen to balance the number of output lines (either analog or digital) on the one hand, versus spatial resolution on the other hand. Placing more APD devices 300 electrically in parallel reduces the number of (analog or digital) output lines, but at the expense of reduced spatial resolution since it is not discernable (either in the analog detection mode or in the digital detection mode) which of the parallel-interconnected APD devices 300 generated a charge pulse.

In general, the number of APD devices 300 placed into electrical parallel should be chosen such that the number of analog output channels comports with PMT-based or other legacy analog detector systems for which the detector array of FIG. 14 is intended to be capable of retrofitting. This can also be done by adding the output signals of several neighboring pixels together, which may be advantageous from a device yield perspective. The digital signals can additionally or alternatively be combined at block/module level. Such combination using application specific integrated circuitry (ASIC) or field programmable gate array (FPGA) combinational circuitry advantageously reduces the number of wires connecting with the coincidence detection block, while not adversely impacting spatial resolution. The detector array of FIG. 14 can be efficiently retrofitted to connect with existing PMT-based analog detector architecture using the "analog out" signal. If the detector architecture is later upgraded to digital mode operation, the detector array of FIG. 14 is readily upgraded simply by making use of the "digital out" signal.

The detector array of FIG. 14 optionally employs a monolithic CMOS die platform 326 that is suitably implemented by fabricating the mixed mode circuitry on a silicon wafer or other silicon substrate using conventional CMOS fabrication techniques and conventional CMOS digital circuit logic for digital components, for example using geometries already described with reference to FIG. 7 or FIG. 8. The detector array illustrated in FIG. 14 can also incorporate other features disclosed herein, such as replacing the illustrated quenching circuitry 324 with active quench-and-recharge circuitry (for example, the active quenching circuit 70" shown in FIG. 4B) so as to provide higher count rates and dynamic range and linearity. As already noted, the transimpedance amplifier 304 amplifies and outputs the analog signal with a defined impedance, thus simplifying external readout circuitry. Optionally, the readout circuitry can be made internal by integration into the monolithic CMOS die platform 326, thus leading to a compact "detector-on-a-chip" system. It is also contemplated to replace the illustrated APD devices 300 by digital silicon photomultiplier devices.

The approach of FIG. 14 is generally applicable to PET, SPECT, CT or other medical imaging modalities that employ single photon counting sensors, as well as for non-medical detector applications such as detectors for astronomy applications and so forth. The detector array of FIG. 14 employs substantial analog aspects and limited switching of digital signals, and accordingly is suitable for use in low electromagnetic emission (EME) applications. Toward this end, it is contemplated to provide switching circuitry (not shown) that switches off at least the digital processing components 310, 312, 314, 320, 322 when the detector array of FIG. 14 is used to output the analog signal "analog out".

The inhibit logic disclosed herein advantageously enables switching off a defective APD device or other photon-counting sensor by removing the bias across the defective device. This reduces the dark current and noise, resulting in a higher signal-to-noise ratio (SNR). Viewed another way, the inhibit logic provides a binary "on/off" bias voltage level control on an individualized detector cell basis for the purpose of reducing dark current.

More generally, the bias voltage over any single photon-counting detector affects the dark current, typically in a super-linear fashion. The dark current also increases with increasing detector temperature. On the other hand, a higher bias voltage produces a high signal level and accordingly higher sensitivity. The SNR is indicative of the tradeoff between detector sensitivity (that is, the "signal" level) and dark current (that is, the "noise" level). At a given detector temperature, there is in general an optimal detector bias voltage that optimizes SNR. This optimal detector bias voltage can be determined empirically, for example using a test set-up similar to those described herein with reference to FIGS. 10-12, or can be determined based on analytical analysis of the p/n junction characteristics of the APD device, or by a combination of empirical and analytical approaches.

Figure 15:
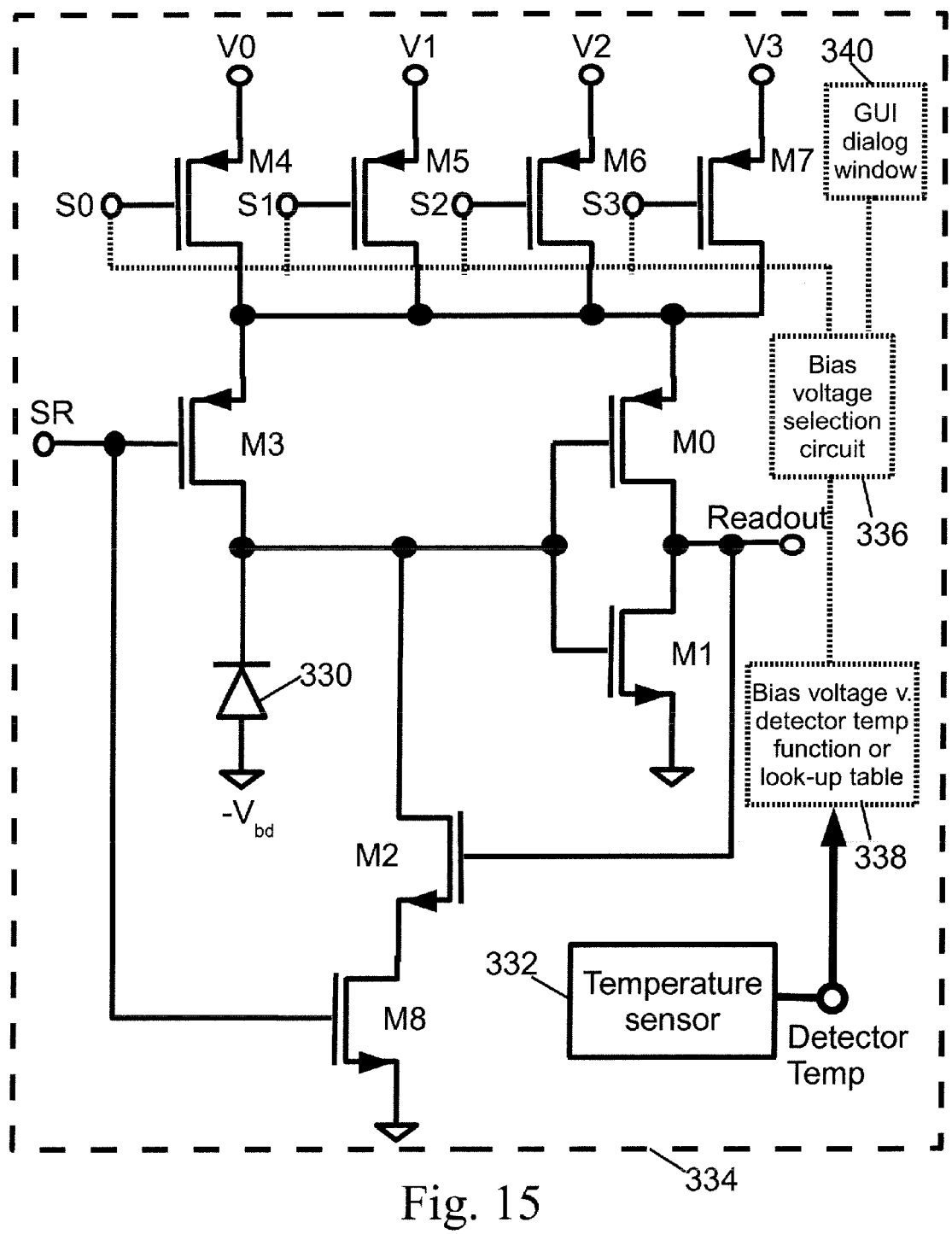
FIG. 15 shows a digital SiPM circuit having a selectable detector bias voltage.

With reference to FIG. 15, a modified digital SiPM bias circuit has an adjustable detector bias that is adjustable amongst any of four bias levels denoted "V0", "V1", "V2", and "V3" where V0<V1<V2<V3 is assumed herein without loss of generality. An avalanche photodiode (APD) detector 330 is read by an inverter-based readout circuit formed by CMOS transistors M0, M1 and connected with the cathode of the APD detector 330. The anode of the APD detector 330 is biased at a voltage $-V_{bd}$ which ensures that the APD detector 330 is in the breakdown region. A p-channel FET M3 is used to increase the detector bias voltage over the APD detector 330 to a value higher than $-V_{bd}$. Switching transistors M4, M5, M6, M7 enable a selected one of four corresponding voltages V0, V1, V2, V3 to be applied via the p-channel FET M3 based on the values of control signals S0, S1, S2, S3 input to the gate terminals of respective switching transistors M4, M5, M6, M7. Only one of the control signals S0, S1, S2, S3 may be at logic 0 at any given time, and the control signal at logic 0 causes the corresponding transistor to apply its corresponding voltage V0, V1, V2, or V3 to the APD detector 330 via the p-channel FET M3. In some embodiments, the condition that only one of the control signals S0, S1, S2, S3 may be at logic 0 at any given time is ensured by an inverting 2-bit decoder connected to a 2-bit memory (not shown), which allows selection of one of the four detector bias voltages V0, V1, V2, V3 for the APD device 330. An n-channel transistor M2 is used to actively quench the diode. A transistor M8 ensures that the APD device 330 is released again during the recharge. The transistor pair M2, M8 can be chained in the CMOS fabrication to more efficiently utilize device area on the CMOS platform. The voltage levels V0, V1, V2, V3 are supplied from one or more external variable voltage sources and can be selected to optimize sensor performance. For example, the voltages V0, V1, V2, V3 can be at equidistant or non-equidistant voltage steps. The voltages are shared by all cells in a pixel. The digital output signal of the inverter formed by transistors M0, M1, denoted "Readout" in FIG. 15, is connected to the readout stage of the cell electronics (not shown). It is also contemplated for one of the selectable detector bias voltage levels, for example V0, to be zero volts which effectively switches off the corresponding APD device or devices 330.

The additional circuitry of the detector bias circuit of FIG. 15 translates into CMOS platform real estate that is used for optically inactive devices (such as transistors M4, M5, M6, M7) and hence reduces the active sensor area. The amount of real estate occupied by the detector bias selection circuitry depends upon the number of selectable detector bias levels (four levels, i.e. V0, V1, V2, V3, in the embodiment shown in FIG. 15). The number of selectable detector bias levels can be chosen to optimize the tradeoff between reduction in active detector area versus improved dark count performance of the APD detectors 330. The latter is also affected by process-induced defect density, p/n junction design, and other factors.

The optimal choice of voltage level is generally temperature-dependent, since as already noted for a given detector temperature there is generally an optimal detector bias voltage that optimizes SNR. The detector temperature is, in some contemplated embodiments, monitored by a suitable temperature sensor 332 that measures a temperature of the CMOS platform 334 on which the CMOS-based sensor array is fabricated. For example, the CMOS platform 334 may in some embodiments be a silicon wafer, optionally bonded to a heat sink, and the temperature sensor 332 can be embodied as a thermocouple, temperature diode, or so forth in thermal communication with the silicon wafer or other CMOS platform 334. As another option, the temperature sensor can be an optically shielded Geiger-mode diode operated at a constant electrical bias, in which case the dark count rate is a measure of temperature. In some such embodiments, the temperature sensor 332 may be a CMOS-based temperature sensor fabricated in monolithic fashion in the CMOS platform 334. In other embodiments, the temperature sensor 332 may be a separate device, such as a conventional thermocouple, that is operatively connected with the CMOS platform 334 by a suitably thermally conductive contact or bond. In either case, the temperature sensor 332 outputs a "Detector Temp" signal that is a voltage, current, or other electrical signal indicative of temperature of the CMOS platform 334, which in turn is expected to be a suitable measure of the temperature of the APD devices 330 monolithically fabricated in the CMOS platform 334. For a plurality of detectors, such as for the one or more rings of detectors 10 of the TOF-PET scanner 8 shown in FIG. 1, a plurality of such temperature sensors 332 may be provided to measure the temperatures at different points along the detector ring or rings, and the measured detector temperature is computed as an average or other statistically representative value of the outputs of the plurality of temperature sensors.

Figure 16:
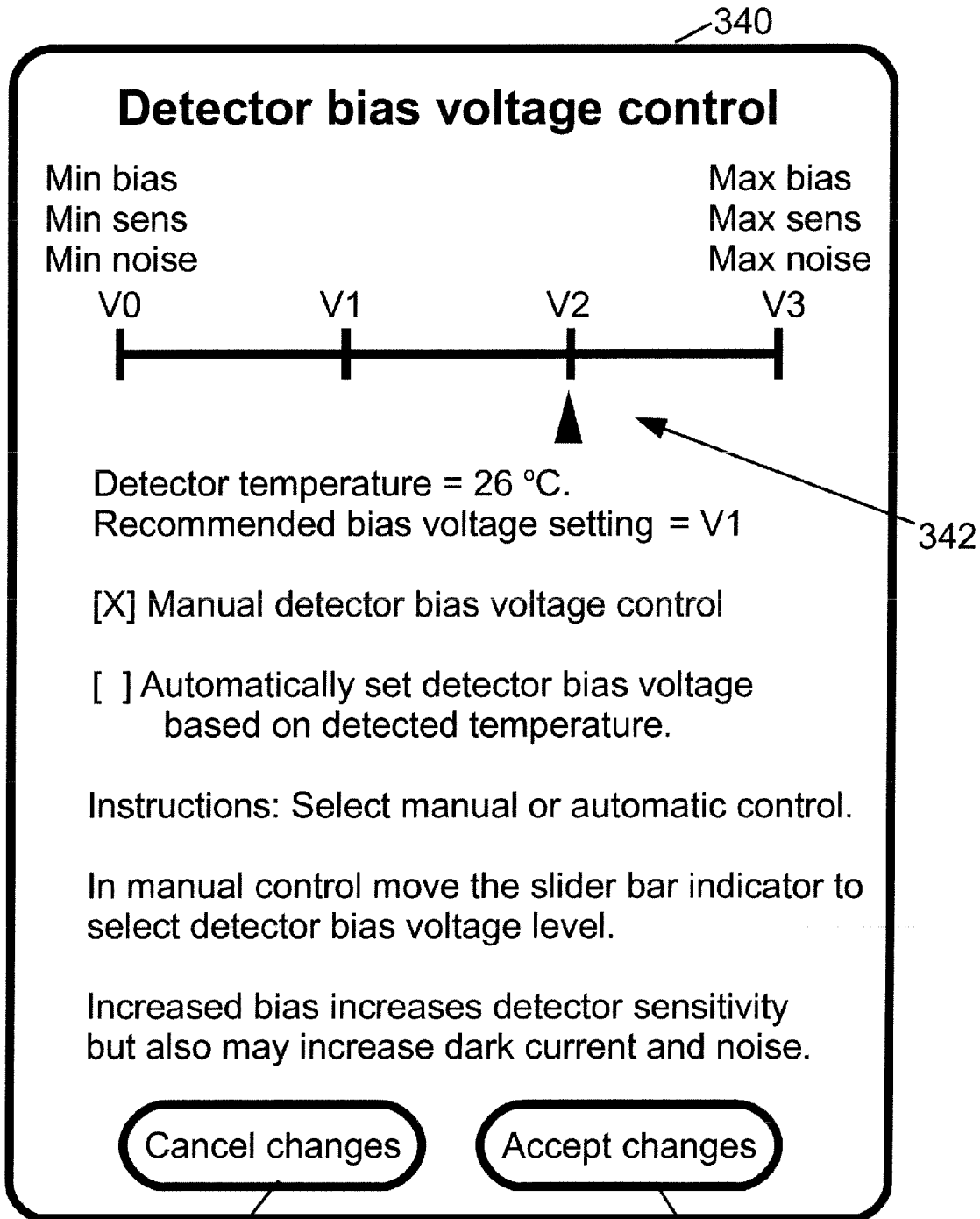
FIG. 16 shows a detector bias voltage control dialog window component of a user interface enabling a user to control detector bias voltage either manually or automatically based on detector temperature.

With continuing reference to FIG. 15 and with further reference to FIG. 16, in some embodiments a selected one of the voltages V0, V1, V2, V3 is applied to the entire set of detectors of the PET, SPECT, or other medical or nonmedical imaging system, such that all detectors are biased at the same selectable voltage level. In this case, a single global detector bias voltage can be selected from the group of voltages V0, V1, V2, V3 (in the case of the illustrative embodiment of FIGS. 15 and 16). This global detector bias voltage can be selected automatically by a bias voltage selection circuit 336, based on the detector temperature output by the temperature sensor 332, or can be manually set by the operator of the PET, SPECT, or other imaging system. For example, as shown in FIG. 15 a bias voltage setting is suitably obtained from a look-up table or mathematical function 338 relating optimal detector bias voltage level to detector temperature. Additionally or alternatively, FIG. 16 illustrates a suitable operator interface for detector bias voltage selection, in which the operator interacts with a detector bias voltage control window 340 (also diagrammatically depicted in FIG. 15) which is a dialog window of a text-based user interface or graphical user interface (GUI, not shown) by which the operator controls the PET, SPECT, or other imaging system. In other embodiments, the user interface may be embodied as a mechanical switch or other user input. The illustrated detector bias voltage control window 340 has two selectable check boxes labeled "Manual detector bias control" and "Automatically set detector bias voltage based on detected temperature", respectively. Only one of the two selectable check boxes is selected at any given time. Instead of check boxes, other suitable GUI user input dialogs can be used, such as a drop-down list, radial button selections, or so forth. At any given time, the detector bias voltage control window 340 displays the currently measured detector temperature along with a recommended detector bias voltage output by the look-up table or mathematical function 338 for the measured current detector temperature. In representative FIG. 16, the current detector temperature is 26° C. and the recommended bias voltage setting is V1, where this is preferably represented by a corresponding numerical voltage level in the window 340. If the automatic control check box is selected, then the detector bias voltage is automatically set to the recommended detector bias voltage, that is, to the detector bias voltage output by the look-up table or mathematical function 338.

In FIG. 15, it should be noted that the blocks 336, 338, 340 are shown in diagrammatic fashion and are in general not monolithically integrated on the CMOS platform 334. It is however contemplated for one or both of the blocks 336, 338 to be monolithically integrated as CMOS digital processing circuitry on the CMOS platform 334. The detector bias voltage control window 340 is typically displayed on the user interface computer 48 shown in FIG. 1, and is not integral with CMOS platform 334. Moreover, it is to be understood that the bias voltage selection circuit 336 may be embodied as a dedicated circuit, such as a dedicated application-specific integrated circuit (ASIC), or as a suitably programmed general-purpose circuit such as a suitably programmed microprocessor or microcontroller, or so forth. Similarly, the look-up table or mathematical function 338 can be variously embodied as a read-only memory (ROM), random access memory (RAM), hard disk or other magnetic storage, or so forth storing the look-up table contents; or may be embodied as a general-purpose circuit such as a microprocessor or microcontroller suitably programmed to evaluate the mathematical function, or so forth.

If the manual detector bias voltage control check box is selected, then a suitable GUI user dialog, such as an illustrated slider bar 342, or a drop-down list of available voltages V0, V1, V2, V3, or so forth, enables the operator to select any one of the four voltages V0, V1, V2, V3. In representative FIG. 16, the manual detector bias voltage control check box is indeed selected, and the operator has set the slider bar 342 to the detector bias voltage setting V2. This operator-selected detector bias voltage setting V2 is higher than the value V1 recommended based on the detector temperature sensor reading, indicating that the operator has elected to enhance sensitivity at the expense of a higher dark current (that is, noise) level.

In the illustrated embodiment, the detector bias voltage control window 340 is a "pop-up" window that is invoked by the operator and displayed (for example, on a display of the user interface computer 48 shown in FIG. 1) whenever the operator wants to adjust the detector bias voltage control or setting. When the user has completed adjustments (for example, selecting either automatic or manual control and, if the latter, selecting the operator-chosen detector bias voltage level) the user can select either: (i) an "accept changes" button 344 that causes the pop-up window 340 to close with the detector bias voltage adjustments saved; or (ii) a "cancel changes" button 346 that causes the pop-up window 340 to close with the detector bias voltage adjustments abandoned.

The detector bias voltage control window 340 is an illustrative example. In some embodiments, no manual control is provided and the sensor temperature-based automatic control is always used—in such embodiments, the detector bias voltage control window 340 is optionally omitted. On the other hand, in some embodiments no automatic control is provided—in such embodiments, the temperature sensor 332 and components of the dialog window 340 relating to automatic detector bias voltage control may be omitted.

The digital SiPM bias circuit of FIG. 15 enables the APD device 330 to be biased at a selected one of the discrete selectable bias levels V0, V1, V2, V3. It is also contemplated, however, to replace the circuitry of FIG. 15 with a single bias voltage source whose output voltage is continuously adjustable, for example using a voltage regulator or a switching power supply. In another contemplated variation, the circuit of FIG. 15 can be employed with one, two, three, or all four of the bias levels V0, V1, V2, V3 being supplied by a bias voltage source whose output voltage is continuously adjustable. In this latter arrangement, the adjustable bias voltage source or sources would typically be adjusted during an initial calibration or periodic re-calibration of the detector system, and thereafter the switching provided by the transistors M4, M5, M6, M7 would be used to switch the currently applied detector bias voltage level as already described herein.

In some embodiments, the bias can be selected individually for every diode in the SiPM pixel. In such embodiments, if some diodes have higher dark counts, the bias voltage can be reduced instead of switching the diode off completely. For example, in one specific approach, the bias V1 is the highest bias, and: (1) all diodes having dark count rates that are less than 10% above the average (or other selected) dark count rate are run at the full bias V1; (2) diodes whose dark count rate (at full voltage V1) exceeds the average dark count rate by between 10% and 20% are biased at a reduced bias V2; (3) diodes whose dark count rate (at full voltage V1) exceeds the average dark count rate by between 20% and 30% are biased at a further reduced bias V3; and (4) diodes whose count rate (at full voltage V1) exceeds the average dark count rate by greater than 30% are biased at a still further reduced bias V4, where in some embodiments V4=0 is contemplated so as to switch off completely these highest dark current diodes. This approach enables one to fine-tune the sensitivity/noise trade-off for a given temperature. When the temperature changes, the biases V1-V4 can be adapted accordingly at a global level.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A photon counting radiation detector comprising:
a Geiger mode detector configured to generate an electrical signal indicative of detection of a photon and dark current noise, the Geiger mode detector including an avalanche photodiode (APD) device biased in an avalanche breakdown region and an output transistor; and
a bias circuit configured to bias the avalanche photodiode at a selectable detector bias voltage level including a lower level at which the detector generates an output with less dark current noise and has less gain and a higher level at which the detector generates an output with more dark current noise and has more gain;
a user interface with which a user selects between an automatic mode and a manual mode, wherein:

in the manual mode, selects among at least (1) the detector output with less dark current noise and less gain and (2) the detector output with more dark current noise and more gain; and
in the automatic mode, the bias circuit automatically adjusts the detector bias voltage level in accordance with a measured detector temperature.

2. The photon counting radiation detector as set forth in claim 1, wherein the Geiger mode detector comprises a plurality of Geiger mode detectors defining a PET detector ring, and the bias circuit is configured to bias the plurality of Geiger mode detectors at a selectable common detector bias voltage level.

3. The photon counting radiation detector as set forth in claim 1, wherein the user interface includes a slider bar via which a user selects the selectable detector bias voltage level.

4. The photon counting radiation detector as set forth in claim 1, wherein the Geiger mode detector and the bias circuit are monolithically fabricated on a common CMOS platform.

5. The photon counting radiation detector as set forth in claim 1, wherein the Geiger mode detector comprises a plurality of Geiger mode detectors defining a detector array, and the bias circuit is configured to bias the plurality of Geiger mode detectors at a selectable detector bias voltage level that varies locally across the detector array.

6. A photon counting radiation detector comprising:
a Geiger mode detector including an array of avalanche photodiodes biased in an avalanche breakdown region and output transistors configured to generate an electrical signal responsive to detection of a photon;
a bias circuit configured to bias the avalanche photodiode at a selectable detector bias voltage level;
a temperature sensor arranged to measure a detector temperature of the Geiger mode detector; and
a bias voltage selection circuit that chooses the selectable detector bias voltage level based on the measured detector temperature,
wherein the temperature sensor includes a diode which is optically shielded against receiving light;
wherein the Geiger mode detector, the optically shielded diode, and the bias circuit are monolithically fabricated on a common CMOS platform.

7. The photon counting radiation detector as set forth in claim 6, wherein the bias voltage selection circuit chooses the selectable detector bias voltage level by referencing a function or look up table relating optimal detector bias voltage and detector temperature.

8. The photon counting radiation detector as set forth in claim 6, wherein the bias circuit is configured to bias the Geiger mode detector in a manual mode under control of a user interface to a selectable one of a plurality of discrete detector bias voltage levels and in an automatic mode selects one of the discrete detector bias voltage levels based on the measured detector temperature.

9. The photon counting radiation detector as set forth in claim 8, wherein the bias circuit includes a plurality of transistors configured to bias the Geiger mode detector at a selectable one of a plurality of discrete detector bias voltage levels based on control signals applied to selected transistors.

10. The photon counting radiation detector as set forth in claim 6, wherein the bias circuit further adjusts the detector bias voltage level of the Geiger mode detector to optimize signal to noise ratio (SNR) of the Geiger mode detector.

11. The photon counting radiation detector as set forth in claim 6, wherein the bias circuit reduces a bias voltage level to selected avalanche photodiodes of the array which have larger dark currents than other avalanche photodiodes of the array to reduce dark counts of the selected avalanche photodiodes.

12. A photon counting radiation detector comprising:
- a Geiger mode detector biased to operate in Geiger mode including a plurality of detector devices connected in parallel and biased to operate in the Geiger mode; and
- readout circuitry operatively connected with the Geiger mode detector, the read out circuitry including:
  - a transimpedance amplifier having an amplifier input connected with the parallel connected detector devices,
  - an analog output connected with an output of the transimpedance amplifier;
  - an integrator circuit connected with an output of the transimpedance amplifier which integrates outputs from the parallel connected detector devices in response to a radiation event;
  - a leading edge discriminator connected with an output of the transimpedance amplifier which outputs a timing signal indicative of a leading edge of the outputs from the parallel connected detector devices in response to the radiation event;
  - digital processing circuitry connected to the integrator and the leading edge discriminator to provide a digital output.

13. The photon counting radiation detector as set forth in claim 12, wherein the Geiger mode detector and the readout circuitry are monolithically integrated on a common CMOS platform.

14. The photon counting radiation detector as set forth in claim 13, wherein on the common CMOS platform, (i) the analog output outputs a distinct current pulse and (ii) the digital output is indicative of the integrated detector device outputs and the leading edge.

15. The photon counting radiation detector as set forth in claim 13, further including:
- time stamp circuitry on the common CMOS platform time stamps detected radiation events based on an output of the leading edge discriminator.

16. The photon counting radiation detection detector as set forth in claim 12, wherein the detector devices include avalanche photodiode (APD) devices.

17. The photon counting radiation detection detector as set forth in claim 12, wherein the detector devices include silicon photomultiplier (SiPM) devices.

18. The photon counting radiation detector as set forth in claim 12, wherein the integrator determines an energy of each detected radiation event and the leading edge discriminator digitally detects radiation event timing.

19. The photon energy counting radiation detector as set forth in claim 12, wherein the Geiger mode detector includes a first block of detector devices and a second block of detector devices and further including:
- circuitry connected with the first and second blocks which outputs the timing signal only in response to both the first and second blocks detecting the photon.

20. A photon counting radiation detector comprising:
- a Geiger mode detector configured to generate electrical signals responsive to detection of photons, the Geiger mode detector including an array of avalanche photodiodes biased to a Geiger mode; and
- a bias circuit configured to bias each of the avalanche photodiodes at a selectable detector bias voltage level, the biasing circuit biases each avalanche photodiode at a selectable voltage, the bias circuit adjusting the bias voltage level on faulty avalanche photodiodes to shut off the faulty avalanche photodiodes and adjusts the bias level of a pattern of non-faulty avalanche photodiodes to shut off or reduce the sensitivity of the pattern of non-faulty avalanche photodiodes to improve a radiation detection uniformity of the detector.

21. A photon counting radiation detector comprising:
Geiger mode detector including an array of avalanche photodiodes, the Geiger mode detector being configured to generate an electrical signal indicative of detection of a photon and dark current noise; and
a bias circuit which biases each avalanche photodiode at a selectable voltage level including a lower level at which the detector generates an output with less dark current noise and has less gain and a higher level at which the detector generates an output with more dark current noise and has more gain, the bias circuit adjusting the bias voltage level on faulty avalanche photodiodes to shut off the faulty avalanche photodiodes and adjusts the bias level of a pattern of non-faulty avalanche photodiodes to shut off or reduce the sensitivity of the pattern of non-faulty avalanche photodiodes to improve a radiation detection uniformity of the detector; and
a user interface with which a user selects between an automatic mode and a manual mode, wherein:
- in the manual mode, selects among at least (1) the detector output with less dark current noise and less gain and (2) the detector output with more dark current noise and more gain; and
- in the automatic mode, the bias circuit automatically adjusts the detector bias voltage level in accordance with a measured detector temperature.

* * * * *